US012414219B2

(12) United States Patent
Snitchler et al.

(10) Patent No.: US 12,414,219 B2
(45) Date of Patent: *Sep. 9, 2025

(54) ION BEAM PATHS ON TARGET SURFACES FOR NEUTRON BEAM GENERATION

(71) Applicant: TAE Technologies, Inc., Foothill Ranch, CA (US)

(72) Inventors: Gregory Luke Snitchler, Foothill Ranch, CA (US); Shahyar Ziaei, Ladera Ranch, CA (US); Harrison Beam Eggers, Pendleton, SC (US); Alejandro Mesa Dame, Indianapolis, IN (US)

(73) Assignee: TAE Technologies, Inc., Foothill Ranch, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/540,447

(22) Filed: Dec. 14, 2023

(65) Prior Publication Data

US 2024/0130032 A1    Apr. 18, 2024

Related U.S. Application Data

(63) Continuation of application No. 17/412,943, filed on Aug. 26, 2021, now Pat. No. 11,889,612.
(Continued)

(51) Int. Cl.
*H05H 7/00* (2006.01)
*A61N 5/10* (2006.01)
*H05H 6/00* (2006.01)

(52) U.S. Cl.
CPC .............. *H05H 7/001* (2013.01); *A61N 5/10* (2013.01); *H05H 6/00* (2013.01);
(Continued)

(58) Field of Classification Search
CPC ...... H05H 7/001; H05H 6/00; H05H 2007/02; H05H 2007/008; A61N 5/10; A61N 2005/109
(Continued)

(56) References Cited

U.S. PATENT DOCUMENTS 4,995,102 A    2/1991    Ichinose et al.
9,849,305 B2   12/2017   Iwata
(Continued)

FOREIGN PATENT DOCUMENTS

EP    1895819    3/2008
EP    3637437    4/2020
(Continued)

OTHER PUBLICATIONS

Thomsen et al., "The Beam Raster System of the European Spallation Source," Presented at Proceedings of the 4th International Workshop on ADSR systems and Thorium, Huddersfield, England, Aug. 30-Sep. 2, 2016, 37 pages.
(Continued)

*Primary Examiner* — Nicole M Ippolito
(74) *Attorney, Agent, or Firm* — ALSTON & BIRD LLP

(57) ABSTRACT

Embodiments of systems, devices, and methods relate to selecting a raster profile for scanning a proton beam across a target. A raster profile is selected from among the plurality of plurality of possible raster profiles based on a value of a figure of merit. A beam is directed across the target surface to form a pattern that is repeated one or more times at different radial orientations to form a scanning profile. A target temperature is monitored while scanning the beam across the target surface according to the scanning profile. The scanning parameters are changeable to avoid target damaging, to improve thermal performance and to optimize particle loading.

20 Claims, 29 Drawing Sheets

Related U.S. Application Data

(60) Provisional application No. 63/070,789, filed on Aug. 26, 2020.

(52) U.S. Cl.
CPC .. *A61N 2005/109* (2013.01); *H05H 2007/002* (2013.01); *H05H 2007/008* (2013.01)

(58) Field of Classification Search
USPC .......................................... 250/492.1, 492.3
See application file for complete search history.

(56) References Cited

U.S. PATENT DOCUMENTS

| | | | |
|---|---|---|---|
| 11,889,612 B2* | 1/2024 | Snitchler | H05H 6/00 |
| 2006/0027544 A1 | 2/2006 | Pailthorp et al. | |
| 2010/0109680 A1 | 5/2010 | Adams et al. | |
| 2012/0264998 A1 | 10/2012 | Fujitaka et al. | |
| 2013/0211390 A1 | 8/2013 | Bor et al. | |
| 2021/0076481 A1 | 3/2021 | Jauregui et al. | |
| 2022/0070994 A1 | 3/2022 | Snitchler et al. | |
| 2023/0284368 A1 | 9/2023 | Dunaevsky et al. | |

FOREIGN PATENT DOCUMENTS

| | | |
|---|---|---|
| JP | 2018201774 | 12/2018 |
| KR | 20180060465 | 6/2018 |

OTHER PUBLICATIONS

Akhmetov et al., "Radially uniform circular sweep of ion beam," Rev. Sci. Instruments, Mar. 2006, 77(3):03C106, 3 pages.

Bayanov et al., "Accelerator-based neutron source for the neutron-capture and fast neutron therapy at hospital," Nucl. Instrum. Methods Phys. Res. A, Aug. 21, 1998, 413(2-3):397-426.

Belchenko et al., "Direct Current H-source for the medicine accelerator (invited)," Rev. Sci. Instruments, May 2004, 75(5):1704-1708.

Kuo et al., "On the development of a 15 mA direct current H-multicusp source," Rev. Sci. Instruments, Mar. 1996, 67(3):1314-1316.

Mardor et al., "The Soreq Applied Research Accelerator Facility (SARAF): Overview, research programs and future plans," Eur. Phys. J. A, May 31, 2018, 54:91, 32 pages.

PCT International Preliminary Report on Patentability in International Appln. No. PCT/US2021/047777, mailed on Mar. 9, 2023, 11 pages.

PCT International Search Report and Written Opinion in International Appln. No. PCT/US2021/047777, dated Mar. 28, 2022, 16 pages.

PCT Invitation to Pay Additional Fees in International Appln. No. PCT/US2021/047777, dated Jan. 5, 2022, 12 pages.

Taskaev, "Accelerator based epithermal neutron source," Phys. Part. Nuclei, Nov. 5, 2015, 46(6):956-990.

Thomsen et al., "The ESS High Energy Beam Transport after the 2013 Design Update," Presented at Proceedings of IPAC 2014, Dresden, Germany, Jun. 15-20, 2014, 2121-2123.

Willis et al., "High-Power Lithium Target for Accelerator-Based BNCT," Presented at Proceedings of the XXIV Linear Accelerator Conference, Victoria, British Columbia, Canada, Sep. 29-Oct. 3, 2008, 223-225.

EP Office Action Mailed on Jul. 28, 2025 for EP Application No. 21786042, 6 page(s).

* cited by examiner

902 ⤴

904 ⤴

906 ↴

908 ↴

ION BEAM PATHS ON TARGET SURFACES FOR NEUTRON BEAM GENERATION

CROSS-REFERENCE To RELATED APPLICATION

This patent application is a continuation (and claims the benefit of priority under 35 USC 120) of U.S. patent application Ser. No. 17/412,943, filed Aug. 26, 2021, which claims priority under 35 U.S.C. 119 to Provisional Application No. 63/070,789, filed Aug. 26, 2020, which is incorporated by reference.

FIELD

The subject matter described herein relates generally to systems, devices, and methods for determining and directing an ion beam path on a target surface, and more particularly determining and directing an ion beam path on a target surface for neutron beam generation.

BACKGROUND

Boron neutron capture therapy (BNCT) is a modality of treatment of a variety of types of cancer, including some of the most difficult types. BNCT is a technique that selectively aims to treat tumor cells while sparing the normal cells using a boron compound. The boron compound allows for efficient uptake by a variety of cell types and selective drug accumulation at target sites, such as tumor cells. Boron loaded cells can be irradiated with neutrons (e.g., in the form of a neutron beam). The neutrons react with the boron to eradicate the tumor cells.

Neutron beams for BNCT can be generated by irradiating a suitable target with an ion beam, such as a proton beam. The ions react with nuclei in the target to emit a beam of neutrons that can be used for BNCT. Exposure of a target to an ion beam for a prolonged period can result in degradation of the target and the resulting neutron beam. Targets can be replaced but may be expensive and result in system down time. Accordingly, a need exists for improved proton beam delivery to prolong a target's functionality below a temperature limit and reduce system down time.

SUMMARY

Example embodiments of systems, devices, and methods described herein relate to a selection of a profile for scanning an ion beam (e.g., a proton beam) across a target surface. In some implementations, a beam path across the target surface forms a first pattern. The pattern, also called a fundamental pattern or cycle, is repeated one or more times at different radial orientations from the first instance of the pattern to form a scanning profile. Here, a "radial" orientation refers to an azimuthal or, alternatively, circumferential direction in a cylindrical coordinate system. The embodiments include at least two instances of a first beam pattern radially offset from each other. The various instances of the beam pattern can be offset by a constant amount such that the scanning profile includes instances of the pattern clocked at regular radial intervals. The embodiments are based on computational modelling configured to improve thermal performance and particle loading, among other advantages. For example, computational modelling can allow for selection of beam scan (or raster) profiles that improve uniformity of particle loading on a target and/or can allow selection of a scanning profile that reduces (e.g., minimizes) peak transient temperature of the target. The computational model indicates the thermal effect on a target of several beam parameters, such as the beam's size and shape. The computational model can include a meshed space encompassing the target. The mesh is composed of a three-dimensional grid in which the thermal loads on the target are modeled. The temperature values are obtained by solving a one-dimensional heat transport equation at each "pixel" (element) of the grid. The one-dimensional heat transport equation is solved for thermal transport through the depth of the pixel considering that cross talk between pixels or lateral heat conduction between pixels is assumed to be negligible. Numerical approaches used to solve the one-dimensional heat transport differential equation include finite-element and finite-difference methods. For either of the finite-element and finite-difference techniques, the target is represented in a plan view as a portion of a grid. The grid can have the same unit cell size in each dimension or the size in each dimension can differ. Resolution can be selected to provide the ability to model beams of different size and structure in line to the physical capabilities of the system under study. The computational model enables selection of a scan profile that defines a path for the proton beam having a minimum delay between successive exposures of a single location of the target to the proton beam exceeds a threshold period. The selected profile can define a path based on a trochoid shape including a plurality of lobes. The computational model enables a selection of a profile that has a varying angular frequency of the proton beam between different lobes of the trochoid shape. The computational model enables a selection of a profile that has a varying angular velocity of the proton beam across the target surface. The computational model enables a selection of a scan profile that has a varying linear velocity of the proton beam across the target surface.

In one aspect, this document describes a method of scanning the beam across a scannable surface of a target along a first path, and scanning the beam across the scannable surface of the target along a second path, wherein the first path forms a first pattern at a first radial orientation, and the second path forms substantially the first pattern at a second radial orientation different from the first radial orientation. The beam can be pulsed while scanning along the first and second paths. The beam continuously propagates while scanning along the first and second paths. The beam moves from an inner region to an outer region of the scannable surface and back to the inner region in the first pattern. The beam moves from an outer region to an inner region of the scannable surface and back to the outer region in the first pattern. The first pattern can include a spiral and a mirror image of the spiral. The first pattern has a first half and a second half, wherein the first and second halves are symmetrical. The first pattern can be continuously curved. The first pattern has a start location and a stop location, wherein the start location can be at or adjacent to the stop location. The first radial orientation differs from the second radial orientation by 180 degrees. The operations can further include: scanning the beam across the scannable surface of the target along a third path, wherein the third path forms the first pattern at a third radial orientation different from the first and second radial orientations. The first, second, and third radial orientations differ by 120 degrees. The operations can further include: scanning the beam across the scannable surface of the target along a fourth path, wherein the fourth path forms the first pattern at a fourth radial orientation different from the first, second, and third radial orientations. The first, second, third, and fourth radial orientations differ by 90 degrees. The operations can further include: scanning the beam across the scannable surface of the target along a fifth path, wherein the fifth path forms the first pattern at a fifth radial orientation different from the first, second, third, and fourth radial orientations. The first, second, third, fourth, and fifth radial orientations differ by 72 degrees. The first path corresponds to a first instance of a cycle, and the second path corresponds to a second instance of the cycle. In some implementations, scanning of the first instance of the cycle and the second instance of the cycle forms a closed loop. The beam can be a proton beam. The scannable surface can be a lithium or beryllium surface. The target generates neutrons when scanned. The beam has a circular cross-sectional profile. The beam has an elliptical cross-sectional profile. The beam has an annular cross-sectional profile. The beam has a hollow cross-sectional profile. The operations performing a boron neutron capture therapy (BNCT). The beam can be generated by a beam system including: an ion source, a first beamline coupled with the ion source, a tandem accelerator coupled with the first beamline, a second beamline coupled with the tandem accelerator, and the target coupled with the second beamline The pattern exposes a majority of the scannable surface to the beam. The second path forms the first pattern at the second radial orientation different from the first radial orientation.

In another aspect, this document describes a method of operating a beam, including: scanning the beam across a scannable surface of a target along a first path, and scanning the beam across the scannable surface of the target along a second path, wherein the first path forms a first pattern at a first radial orientation, and the second path forms a second pattern at a second radial orientation different from the first radial orientation, wherein the first and second patterns are substantially the same but for the different radial orientations. The first and second patterns are the same but for the different radial orientations.

In another aspect, this document describes a beam system including: a computing device including a processor communicatively coupled with memory, wherein the memory stores a plurality of instructions that, when executed by the processor, cause the processor to: control movement of a beam across a scannable surface of a target along a first path, and control movement of the beam across the scannable surface of the target along a second path, wherein the first path can include a first pattern at a first radial orientation, and the second path can include substantially the first pattern at a second radial orientation different from the first radial orientation. The first path traverses from an inner region to an outer region of the scannable surface and back to the inner region in the first pattern. The first path traverses from an outer region to an inner region of the scannable surface and back to the outer region in the first pattern. The first pattern can include a spiral and a mirror image of the spiral. The first pattern can include a first half and a second half, wherein the first and second halves are symmetrical. The first pattern can be continuously curved. The first pattern can include a start location and a stop location, wherein the start location can be at or adjacent to the stop location. The first radial orientation differs from the second radial orientation by 180 degrees. The plurality of instructions, when executed by the processor, further cause the processor to: control movement of the beam across the scannable surface of the target along a third path, wherein the third path can include the first pattern at a third radial orientation different from the first and second radial orientations. The first, second, and third radial orientations differ by 120 degrees. The plurality of instructions, when executed by the processor, further cause the processor to: control movement of the beam across the scannable surface of the target along a fourth path, wherein the fourth path can include the first pattern at a fourth radial orientation different from the first, second, and third radial orientations. The first, second, third, and fourth radial orientations differ by 90 degrees. The system plurality of instructions, when executed by the processor, further cause the processor to: control movement of the beam across the scannable surface of the target along a fifth path, wherein the fifth path can include the first pattern at a fifth radial orientation different from the first, second, third, and fourth radial orientations. The first, second, third, fourth, and fifth radial orientations differ by 72 degrees. The plurality of instructions, when executed by the processor, further cause the processor to: control movement of the beam across the scannable surface of the target along a sixth path, wherein the sixth path can include the first pattern at a sixth radial orientation different from the first, second, third, fourth, and fifth radial orientations. The first, second, third, fourth, fifth, and sixth radial orientations differ by 60 degrees. The beam can be a proton beam. The scannable surface can be a surface of a lithium layer or beryllium layer. The target generates neutrons when scanned. The beam can include a circular profile. The beam can include an elliptical profile. The beam can include an annular profile. The beam can include a hollow profile. The operations are performed in boron neutron capture therapy (BNCT). The beam can be generated by a beam system including: an ion source, a first beamline coupled with the ion source, a tandem accelerator coupled with the first beamline, a second beamline coupled with the tandem accelerator, and the target coupled with the second beamline. The first pattern exposes a majority of the scannable surface to the beam. The second path forms the first pattern at the second radial orientation different from the first radial orientation.

In another aspect, this document describes a computer-implemented method for selecting a raster profile for scanning a proton beam across a target, the method including: establishing, using a computer processing system, a plurality of possible raster profiles for scanning the proton beam across the target, each of the plurality of possible raster profiles including one or more beam parameters, each of the one or more beam parameters characterizing a property of the proton beam and one or more path parameters characterizing a path of the proton beam across the target, establishing, using the computer processing system, one or more target parameters characterizing the target, calculating, using the computer processing system, a value of a figure of merit for each of the possible beam raster profiles, wherein the figure of merit can be based on a thermal loading of the target by the proton beam for the corresponding possible raster profile, selecting, using the computer processing system, a raster profile from among the plurality of plurality of possible raster profiles based on the value of the figure of merit, and directing the proton beam across the target according to the selected raster profile. Calculating the values for the figure of merit can include, for each of the possible raster profiles, calculating a thermal load at each of a plurality of discrete portions of the target based on a linear relationship between the thermal load and a proton flux at each discrete portion for the corresponding raster profile. Each discrete portion corresponds to an area of a surface of the target in the path of the proton beam that can be smaller than a dimension of the proton beam. The thermal load at each discrete portion can be calculated based on heat transfer through a depth of the target away from a surface of the target on which the proton beam can be incident. The figure of merit can be selected from the group consisting of: a peak temperature of the target, a temperature change of the target, an average temperature of the target, and a usage efficiency of the target. The one or more beam parameters are selected from the group consisting of: a beam dimension, a beam shape, and a beam structure. The beam dimension can be in a range from 10 mm to 30 mm. The beam shape can be circular or elliptical. A structure of the beam can be circular or annular. The one or more path parameters can be selected from the group consisting of: a frequency associated with the path of the proton beam, a linear velocity of the proton beam across a surface of the target, a number of radial scan layers in a super cycle of the path of the proton beam, and a number of super cycles of the path of the proton beam. The one or more target parameters are selected from the group consisting of: target surface area, target thickness, and target composition. The target can include a layer of lithium or a layer of beryllium. The target can include a layer of a metal supporting the layer of lithium or the layer of beryllium. Selecting can include presenting an operator of the proton beam with a list of the possible raster profiles and receiving, via the computer system, a selection from the list by the operator. The operations can further include measuring one or more properties of the target and selecting the raster profile based on the measured property of the target. The one or more properties of the target comprise a temperature of the target at one or more locations on the target. The operations, can further include measuring one or more properties of the beam and selecting the raster profile based on the measured property of the beam. The one or more properties of the beam are measured upstream from the target. The selected raster profile defines a path for the proton beam having a minimum delay between successive exposures of a single location of the target to the proton beam exceeds a threshold period. The selected raster profile defines a path based on a trochoid shape. The trochoid shape can include a plurality of lobes. The angular frequency of the proton beam varies for different lobes of the trochoid shape. The selected raster profile can include a varying angular velocity of the proton beam across the target surface. The selected raster profile can include a varying linear velocity of the proton beam across the target surface.

In another aspect, this document describes a computer-implemented method including: monitoring a temperature of a target while scanning a proton beam across a surface of the target according to a first raster profile, and based on the monitored temperature, changing the scanning from the first raster profile to a second raster profile, wherein the second raster profile and the first raster profile result in differing heating profiles of the target according to a computer model of a thermal loading of the target by the first and second raster profiles. The scanning can be changed in response to selection of the second raster profile from among a plurality of raster profiles by a human operator of the proton beam. The scanning can be changed automatically according to a feedback or feedforward algorithm. The temperature can be monitored at multiple discrete locations of the target. The temperature can be monitored by obtaining a thermal image of the target.

In another aspect, this document describes a method of operating a beam, including scanning a charged particle beam across a scannable surface of a target in a super cycle, wherein the super cycle can include a plurality of cycles, each cycle of the plurality of cycles having the same shape and a different azimuthal orientation, wherein the plurality of cycles are concatenated together such that a path of the charged particle beam traverses the plurality of cycles in a closed loop. The plurality of cycles can include two cycles azimuthally offset by 180 degrees from each other. The plurality of cycles can include three cycles azimuthally offset by 120 degrees from each other. The plurality of cycles can include four cycles azimuthally offset by 90 degrees from each other.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein and be protected by the accompanying claims. In no way should the features of the example embodiments be construed as limiting the appended claims, absent express recitation of those features in the claims.

BRIEF DESCRIPTION OF DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

Like reference symbols in the various drawings indicate like elements.

DETAILED DESCRIPTION

Figure 1A:
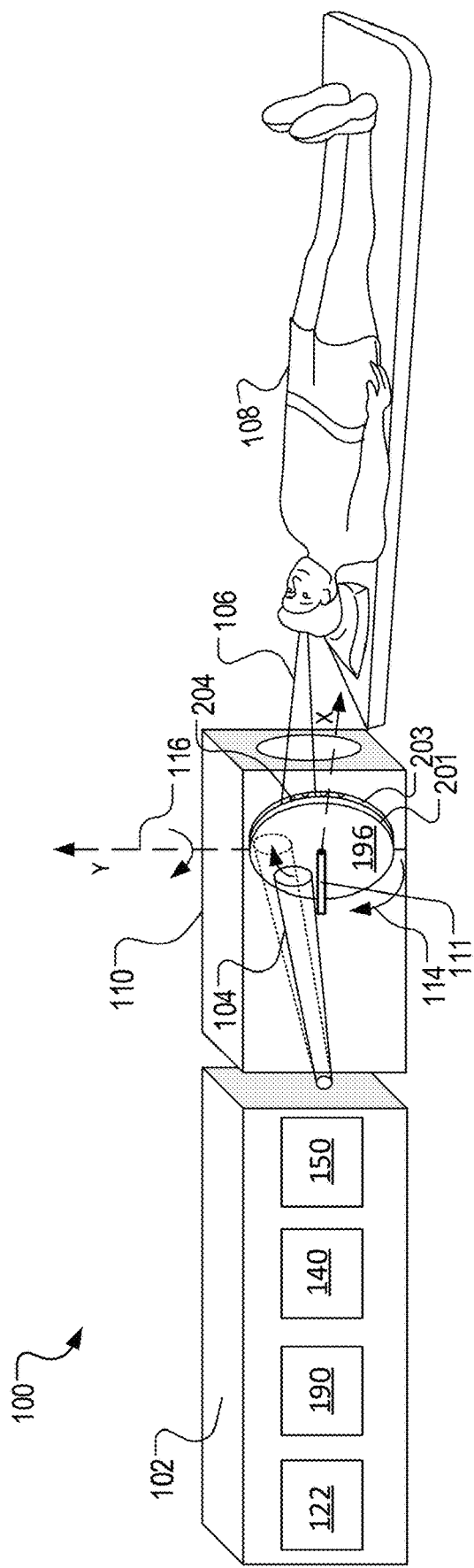
FIG. 1A is a schematic view of an example embodiment of a neutron beam system in accordance with the present disclosure.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The term "particle" is used broadly herein and, unless otherwise limited, can be used to describe an electron, a proton (or H+ ion), or a neutron, as well as a species having more than one electron, proton, and/or neutron (e.g., other ions, atoms, and molecules).

Example embodiments of systems, devices, and methods are described herein for beam paths of a beam along a target surface of, or used in combination with, a beam system (e.g., including a particle accelerator). The embodiments described herein can be used with any type of particle accelerator or in any particle accelerator application involving production of a charged particle beam at specified energies for supply to the particle accelerator. Embodiments herein can be used in numerous applications, an example of which is as a neutron beam system for generation of a neutron beam for use in boron neutron capture therapy (BNCT). BNCT uses a beam of epithermal neutrons (e.g., with an energy spectrum within 3-30 kiloelectronvolts) for cancer treatment. In some implementations, the epithermal neutrons (e.g., epithermal neutron beams) are generated based on nuclear reactions of protons (e.g., a proton beam) with either a Beryllium target or a Lithium target.

The proton beam can be generated by a particle accelerator, such as a tandem accelerator. For example, the tandem accelerator can be an electrostatic accelerator that employs a two-step acceleration of charged particles using a single high voltage terminal. The high voltage can be used to generate an electric field that is applied to the incoming beam of negatively charged ions to accelerate it towards the center of the accelerator. The center of the tandem accelerator can be configured to convert the beam of negatively charged ions into a proton beam in a process of charge exchange. The parameters of the proton beam, such as a beam dimension, a beam shape, and a beam structure can be varied to optimize target usage relative to localized heating of the target.

For ease of description, many embodiments described herein will be done so in the context of scanning a proton beam across a target to generate a neutron beam for use in BNCT, although the embodiments are not limited to such, and can be applied to scanning of other charged particle beams, generation of beams other than neutron beams, and usages outside of BNCT applications. The target can be maintained in a fixed (unvarying) position while scanning the proton beam across the target surface. Alternatively, the target can be moved (e.g., rotated) while the proton beam is scanned across the target surface. Both approaches are described herein. The embodiments pertaining to the scanning (rastering) of charged particle beams are described primarily in the context of a fixed target; however all such embodiments can be configured for use in the approach where the target is moving.

FIG. 1A illustrates a schematic view of an example embodiment of a system 100 for use in BNCT, in accordance with the present disclosure. The system 100 includes a beam system 102 configured to generate a proton beam 104 and a target 196 that is scanned by the proton beam 104 to generate a neutron beam 106 that is directed towards a patient 108. The beam system 102 includes a charged particle source 122, a low-energy beamline (LEBL) 190, an accelerator 140 and a high-energy beamline (HEBL) 150. The accelerator 140 is coupled to the low-energy beamline (LEBL) 190 and is configured to accelerate a charged particle (proton) beam. The high-energy beamline (HEBL) 150 extends from the accelerator 140 to a target assembly 110 housing a target 196 onto which the charged particle beam can be directed. LEBL 190 is configured to transport the beam from source 122 to the accelerator 140. The accelerator 140 is configured to accelerate the beam. HEBL 150 transfers the beam 104 from an output of accelerator 140 to the target 196. In some implementations, the HEBL 150 transfers the beam 104 to the target 196 through a target chamber of the target assembly 110. The beam 104 can be a negative charged particle beam or a positive charge particle beam. The target 196 can be a device that converts the charged particle beam 104 into another type of particle beam 106, such as a neutral beam, can be a workpiece, or other body onto which the charge particle beam is directed for useful purpose, such as an irradiating target of a patient 108.

Figure 1B:
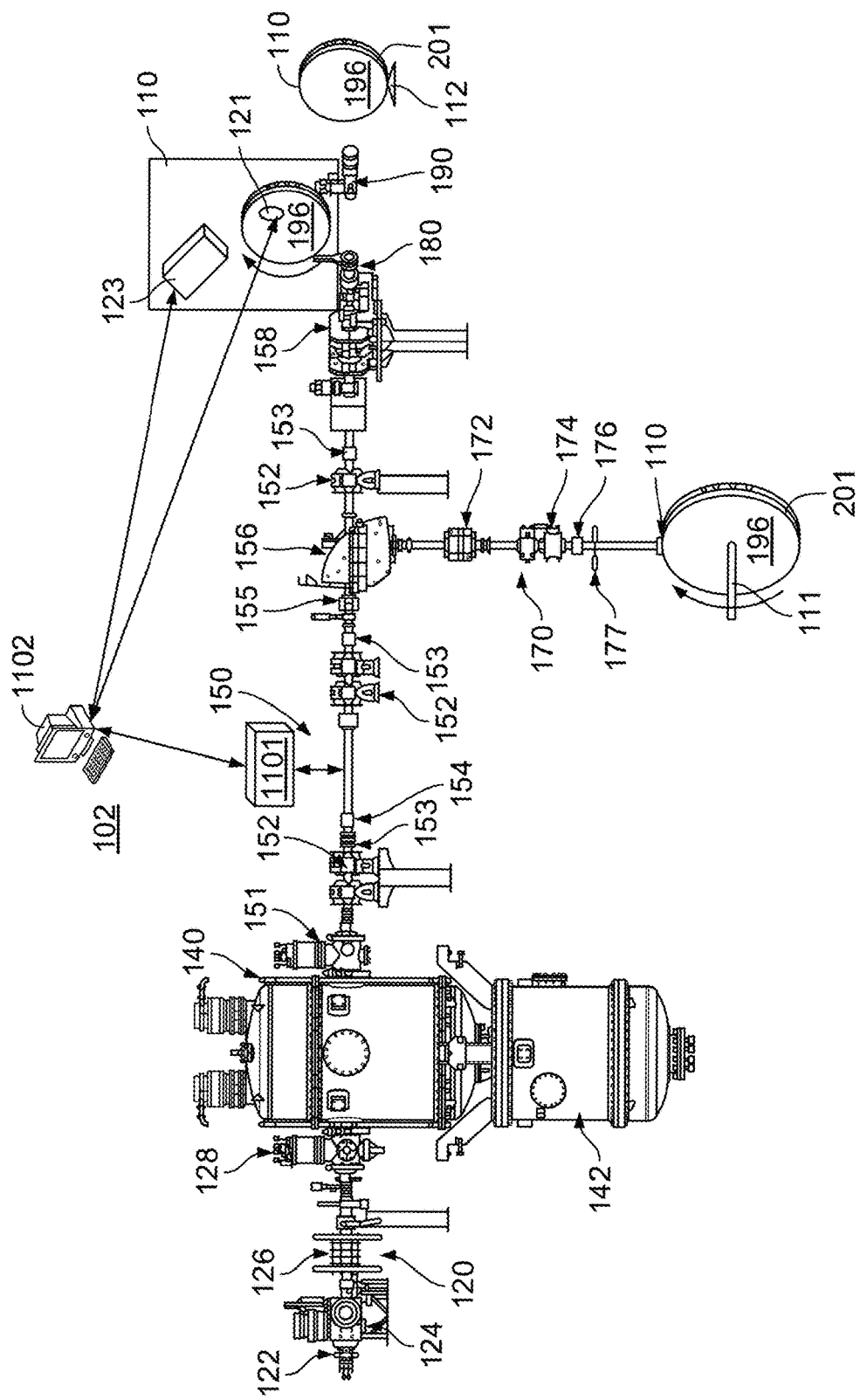
FIG. 1B is a schematic view of an example embodiment of a neutron beam system for use in boron neutron capture therapy (BNCT).

FIG. 1B is a schematic view illustrating an example embodiment of the beam system 102 configured as a neutron beam system for use in BNCT. The beam system 102 includes a pre-accelerator system 120 forming at least a portion of the LEBL, where the pre-accelerator system 120 serves as a charged particle beam injector, a high voltage (HV) tandem accelerator 140 coupled to the pre-accelerator system 120, and a high-energy beamline 150 extending from the HV tandem accelerator 140 to a neutron target assembly 110 housing a neutron-producing target 196, as described with reference to FIG. 1A. The beam system 102 as well as pre-accelerator system 120 can also be used for other applications, such as cargo inspection and applications, and is not limited to BNCT.

The pre-accelerator system 120 (also referred to herein as the charged particle beam injector or ion beam injector) can be configured to transfer the ion beam from an ion source 122 to an input (e.g., an input aperture) of the HV tandem accelerator 140. The pre-accelerator system 120 can include the ion source 122 (e.g., negative ion source), a turbomolecular pump 124 (e.g., an ion source vacuum chamber for removing gas), a pre-acceleration tube 126, and a pump chamber 128. In some implementations, the beam source 122 can include a negative ion source. The pre-accelerator system 120 can be configured to provide acceleration of the beam particles to energy levels required for the HV tandem accelerator 140, and to provide an overall convergence of the negative ion beam to match an input aperture area at an input aperture or entrance of the HV tandem accelerator 140. The pre-accelerator system 120 can be configured to minimize or defocus backflow as it passes from the HV tandem accelerator 140 through the pre-accelerator system 120 in order to reduce the possibility of damage to ion source 122 and/or the backflow reaching the filaments of the ion source 122.

The HV tandem accelerator 140 is powered by a high voltage power supply 142 coupled thereto. The HV tandem accelerator 140 includes a vacuum tank, a charge-exchange target, accelerating electrodes, and a high voltage feedthrough. The HV tandem accelerator 140 can, in some implementations, accelerate a hydrogen beam to produce a proton beam with an energy generally equal to twice the voltage applied to the accelerating electrodes positioned within the HV tandem accelerator 140. The energy level of the proton beam can be achieved by accelerating the beam of negative hydrogen ions from the input of the HV tandem accelerator 140 to the innermost high-potential electrode, stripping two electrons from each ion, and then accelerating the resulting protons downstream by the same voltages encountered in reverse order.

The high-energy beamline 150 can transfer the proton beam from the output of the HV tandem accelerator 140 to the neutron-generating target 196 in the neutron target assembly 110 positioned at the end of a branch 170 of the beamline extending into a patient treatment room.

The beam system 102 can be configured to direct the proton beam to one or more targets 196 and associated target areas. In some implementations, the high-energy beamline 150 includes multiple (e.g., three) branches 170, 180, and 190 configured to extend to multiple different patient treatment rooms. The branches 180 and 190 can contain target assemblies similar to branch 170. The high-energy beamline 150 includes a pumping chamber 151, quadrupole magnets 152 and 172 to prevent de-focusing of the beam, dipole or bending magnets 156 and 158 to steer the beam towards one or more targets, beam correctors 153, diagnostics such as current monitors 154 and 176, fast beam position monitor 155 section, and a scanning magnet 174.

The beam system 102 may employ one or more control systems 1101 with which one or more computing devices 1102 may communicate in order to interact with the systems and components of the beam system 102 (e.g., neutron beam system 102). In some implementations, the computing device 1102 is configured to execute a computational model that enables selection of a raster profile, as described with reference to FIGS. 5A and 5B. The computing device 1102 is configured to receive a user input including a selection of one or more parameters of the target scanning process. The parameters can define the raster profile including the beam path, the orientation of a shaped beam relative to the scannable surface of the target, the beam cross-sectional profile, and the beam velocity. The parameters can define target characteristics, such as rotation of the target 196 (e.g., angular velocity of the target). The raster path as used herein does not imply any particular beam path (e.g., such as moving only in orthogonal directions). In some implementations, the computing devices 1102 are configured to receive a real time signal measured by a sensor 121 or a thermal camera 123, which are used to adjust in real time the raster profile using an adaptable scanning program to avoid local overheating of the target 196 (e.g., keeping the local temperature below Lithium melting temperature of 180° C.). The one or more thermal sensors 121 can detect localized temperature corresponding to a portion of the target. The thermal camera 123 can be configured to generate a signal that can be processed to generate a temperature map of the target 196. The computing device 1102 can be configured to process the received input and generate a set of scanning parameters that are transmitted to the one or more control systems 1101 to control the target scanning process.

The design of the high-energy beamline 150 depends on the configuration of the treatment facility (e.g., a single-story configuration of a treatment facility, a two-story configuration of a treatment facility, and the like). The beam can be delivered to a target assembly 110 (e.g., positioned near a treatment room having a patient 108) with the use of the bending magnet 156. Quadrupole magnets 172 can be included to then focus the beam to a certain size at the target. The beam can pass one or more scanning magnets 174, which provide lateral movement of the beam onto the target surface in a desired pattern (e.g., spiral, curved, stepped in rows and columns, combinations thereof, and others). The beam lateral movement can enable generation of smooth and even time-averaged distribution of the proton beam on the target 196, preventing overheating of the target 196 and making the particle (e.g., neutron) generation as uniform as possible within the target layer 201 (e.g., lithium layer).

The scanning magnets 174 can be configured to direct the beam to a current monitor 176, which measures beam current. The beam current value, measured by the current monitor 176, can be used to operate a safety interlock. The target assembly 110 can be physically separated from the high-energy beamline volume with a gate valve 177. A function of the gate valve 177 is to separate the vacuum volume of the beamline from the target 196 during target exchange/loading. In some implementations, the beam instead of being bent by 90 degrees by a bending magnet 156, can be directed straight to the right to enter the quadrupole magnets 152, which are located in the horizontal beamline The beam could be bent by another bending magnet 158 to a preset angle, depending on a setting requirement (e.g., location of a patient or a room configuration). In some implementations, bending magnet 158 can be arranged at a split in the beamline and can be configured to direct the beam in one of two directions for two different treatment rooms located on the same floor of a medical facility.

Figure 2A:
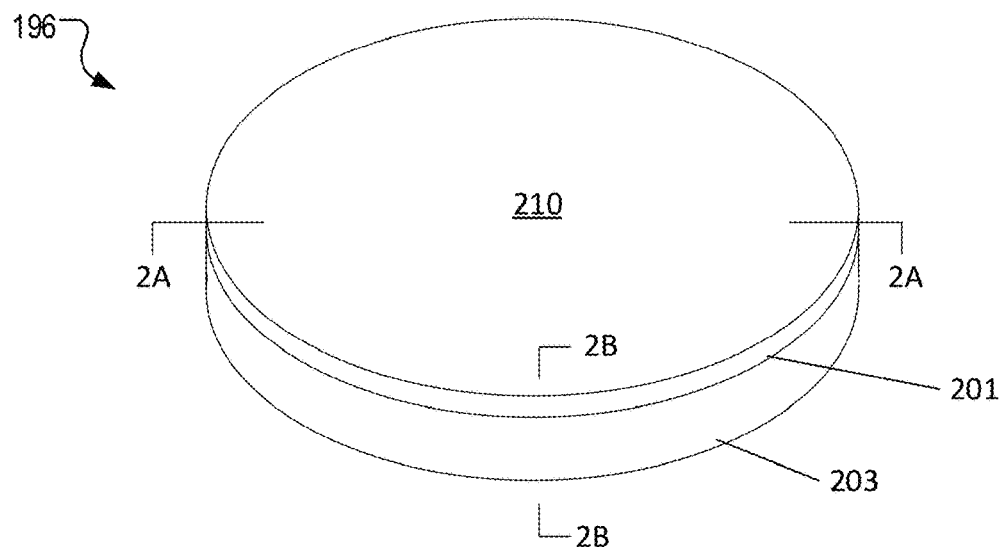
FIG. 2A is a perspective view of an example embodiment of a target.
Figure 2B:
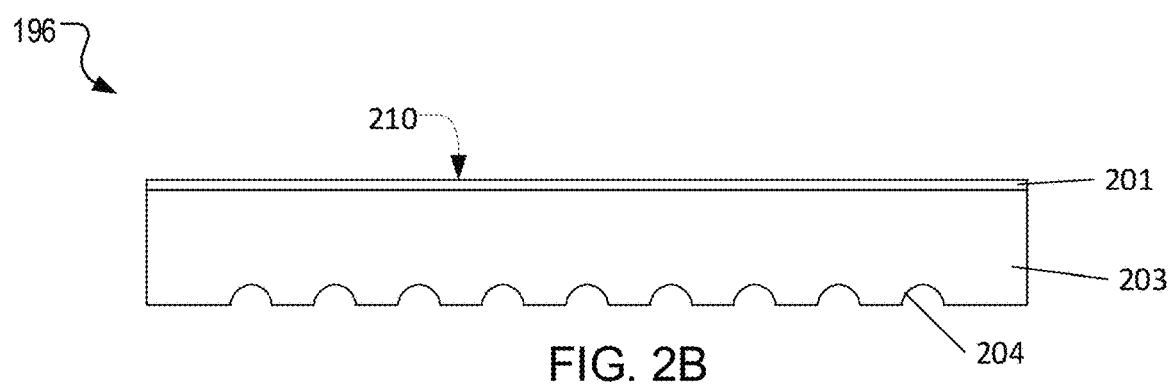
FIG. 2B is a cross-sectional view taken along line 2B-2B of FIG. 2A.

FIG. 2A is a perspective view of the target 196 and FIG. 2B is a cross-sectional view of the target 196 illustrating cooling channels. In this embodiment target 196 is disk shaped with a generally circular outer profile. The target 196 generally includes one or more target layers 201 supported by a substrate 203. The side of the substrate 203 includes channels 204 for a coolant. A scannable surface 210 is present on target layer 201, which is the surface of target layer 201 that can be scanned by the proton beam to produce neutrons. The target layers 201 include a neutron source layer, such as a layer of lithium, beryllium, or other suitable material that interacts with the proton beam 104 to produce a neutron flux. The thickness and composition of the one or more target layers 201 can vary depending on the properties of the proton beam and the desired neutron flux. For example, a lithium based target layer can have a thickness in a range from about 10 microns ($\mu m$) to about 400 $\mu m$. The target layer 201 can be adhered to the substrate 203 via a thermal bond.

The substrate 203 can include one or more layers of copper, aluminum, stainless steel, titanium, and/or molybdenum. The target layer 201, including a reactive metal, can form an amalgam with the substrate 203. The characteristics of the target 196 (e.g., layer thickness, composition, and bond type) are associated with an onset of blistering at particular levels of particle doses per target surface.

Channels 204 can be used to circulate coolant across the backside of substrate 203 during operation of the system 100, in order to dissipate heat produced by absorption of kinetic energy from slowing in substrate 203 of the protons that did not participate in the reaction. Alternatively, or additionally, coolant can be provided as a fluid chamber in contact with at least a portion of the substrate 203. For example, coolant channels can be formed as capped throughholes that cross the substrate 203 and define closed fluid passages with a variety of different geometries (e.g., circular or rectangular cross sections) and dimensions (e.g., cross sectional diameters ranging from about 0.5 millimeters (mm) to about 3 mm).

The target 196 can be supported by a support structure (e.g., a shaft 111 or a base 112). The support structure can be configured to maintain the target 196 in a fixed position or to rotate the target 196 clockwise 114 or counterclockwise (CCW) in a vertical plane including a vertical axis 116 that is nominally perpendicular to the beam axis. The particle beam 104 can be dynamically directed towards the target 196 according to a particular pattern (e.g., spiral, curved, stepped in rows and columns, combinations thereof, and others) that may change over time. The pattern can be repeated at a given frequency. In some implementations, both the target 196 and the beam 104 move relative to the beam axis during operation, such that segments of the rotatable target 196 can be sequentially contacted by the beam 104 to form a scanning pattern, as described in detail with reference to FIGS. 3A-3C, 4A-4G, and 7A-7F. As a result of the interaction of the beam 104 with the target layer 201 (e.g., neutron source layer), a beam 106 (e.g., neutron beam) is generated and directed (e.g., via a collimator or other beam-shaping structure) towards a treatment area of the patient 108.

Figure 2C:
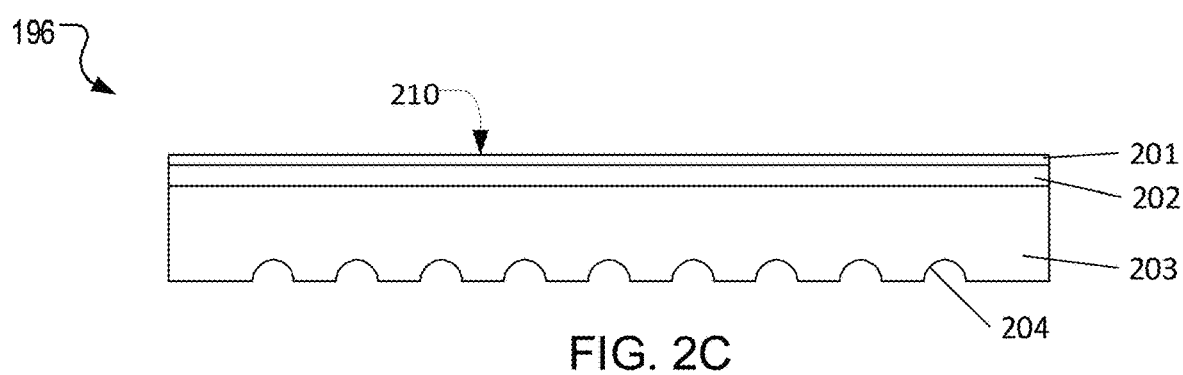
FIG. 2C is a cross-sectional view of another example embodiment of a target.

FIG. 2C is a cross-sectional view of another example embodiment, where target 196 includes an intermediate layer 202 located between the target layer 201 and the target substrate 203. The intermediate layer 202 can reduce the likelihood of blister formation within the target 196 due to the impingement of the beam. The intermediate layer 202 can be composed of thermally conductive materials that are resistant to blistering, such as tantalum.

During operation of the beam system 102, the proton beam 104 is directed at scannable surface 210 of target 196. In order to avoid overheating, the proton beam 104 is moved at a rapid rate in two or more directions (e.g., X and Y) across surface 210, which is a process referred to as scanning. The path that the beam takes across surface 210 determines the amount of heating that occurs at different locations across surface 210 and relative differences in particle loading on target 196. The beam path can be conformed to the capabilities of the system to cool the target 196 and the capability of the target 196 to withstand variances in particle loading.

Figure 3A:
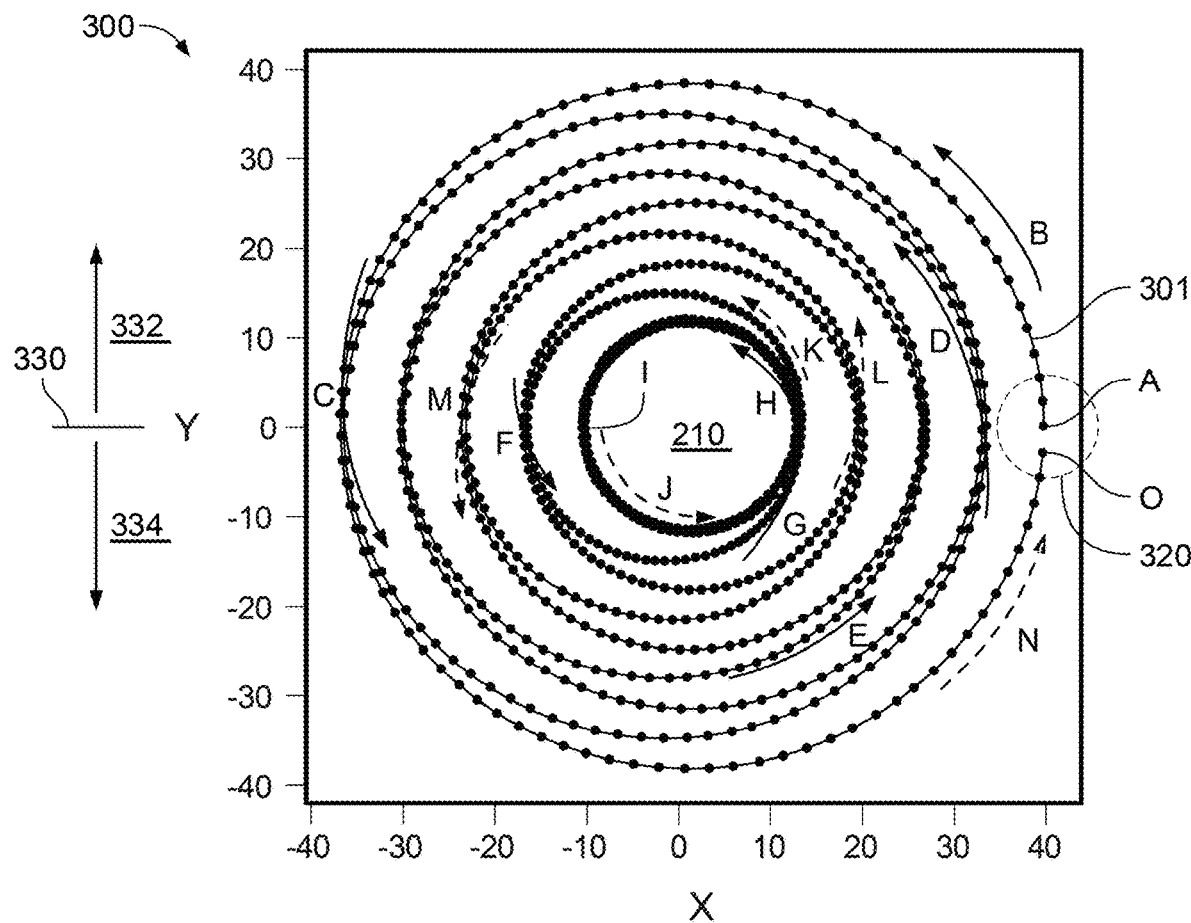
FIG. 3A is a schematic view of an example of a beam path that forms a first pattern in accordance with the present subject matter.

FIG. 3A is a schematic view depicting an example pattern 300 formed by a path 301 that a beam takes across surface 210. The outer boundary of the beam cross-section is indicated by cross-sectional profile 320, which in this example is circular. Pattern 300 of path 301 is curved with multiple loops, or orbits, created as the beam proceeds from an outer region of surface 210 to an inner region and then back again to the outer region. Beam path 301 includes a starting location A and a stopping location O. The locations A, O can be the same single location or different locations. In some embodiments, the starting and stopping locations A, O can be the same position or in close proximity to each other (e.g., adjacent positions, or positions within one beam diameter of each other).

Path 301 starts at location A and proceeds in a CCW manner indicated by arrow B. Path 301 continues in an inwardly directed spiral fashion (e.g., with continually decreasing radius) as indicated by arrows C, D, E, F, G, and H. Arrow H indicates entry of beam path 301 into the smallest radius orbit until reaching location I, which marks the position where the beam path radius transitions from a continually decreasing radius to a continually increasing radius. In other words, at location I, beam path 301 begins to transition from the inner region of surface 210 back towards the outer region. Arrow J indicates the path of beam 301 from location I in counterclockwise manner in an outwardly directed spiral fashion (e.g., with continually increasing radius) as indicated by arrows K, L, M, and N until reaching stopping location O. At this point path 301 has completed a transition from the outer region to the inner region and back to the outer region of surface 210. A path with at least one orbit about a central point, that has a starting and a stopping location at the same distance (or radius) from the central point, and that traverses between a minimum distance (or radius) from the central point and a maximum distance (or radius) from the central point, is referred to as a cycle. The starting and stopping locations can be at any distance between (and including) the minimum distance and the maximum distance. In this case, the single cycle forms a closed loop such that stopping location O is substantially at or adjacent to starting location A.

Pattern 300 can cover a majority of the surface area of the scannable surface 210 of the target. In this example beam profile 320 is large enough such that area of surface 210 impinged upon by the beam will overlap as the beam transitions through each orbit. Stated differently, the width of beam profile 320, measured perpendicular to the direction of travel of the beam, is greater than a distance between adjacent orbits. The pattern 300 is symmetrical along axis 330, such that a first half 332 of pattern 300 is a mirror image of a second half 334 of pattern 300. The outward to inward portion of path 301 from location A to location I is a mirror image of the inward to outward portion of path 301 from location I to location O.

While path 301 is described as transitioning in a CCW fashion, from the outer region to the inner region and back, the embodiments described herein are not so limited. For example, in some implementations, the beam can utilize a path that follows a clockwise (CW) rotation starting at the inner region, transitioning to the outer region and then back to the inner region (one cycle). Path 301 can complete an entire cycle or only a portion of a cycle, for example, involving a transition from the inner region to the outer region or the reverse.

Figure 3B:
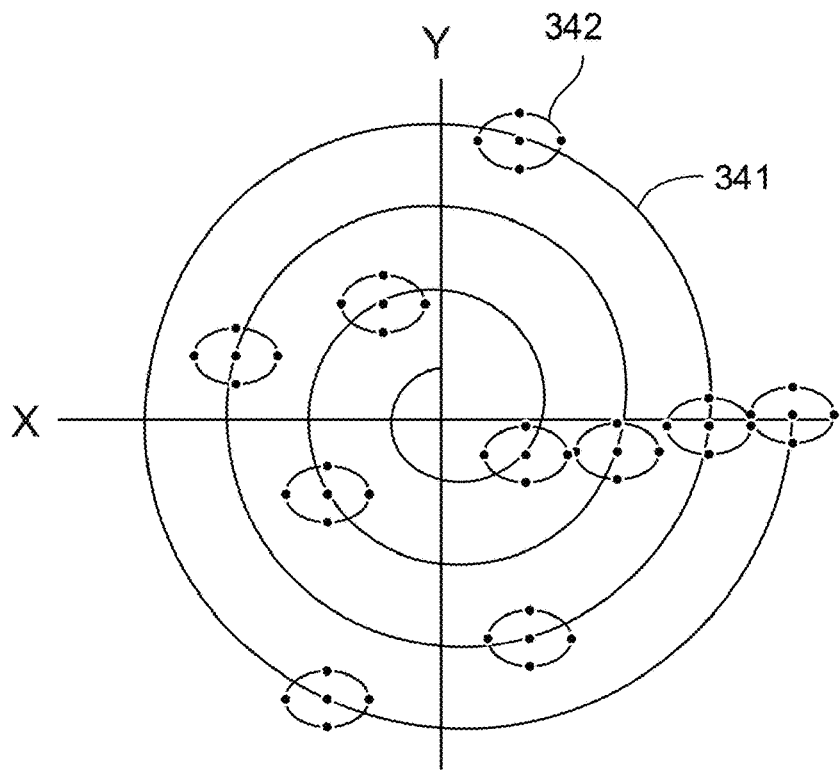
FIGS. 3B-3C are schematic views of example beam paths with elliptical and circular beam cross-sectional profiles, respectively.
Figure 3C:
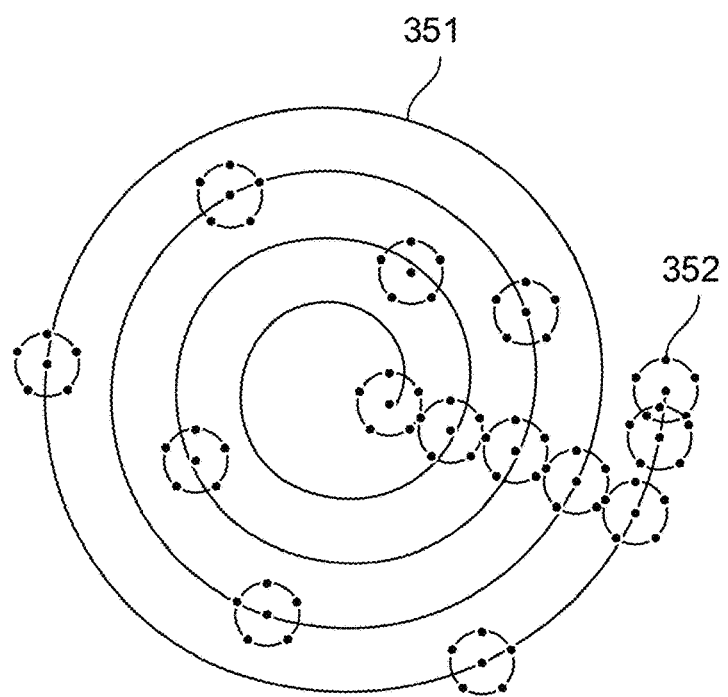

FIGS. 3B and 3C are schematic views depicting examples of different paths taken with different beam cross-sectional profiles. In FIG. 3B, an elliptical (e.g., oval) beam profile 342 having a greater X dimension than Y dimension follows a path 341 sized such that the beam cross-sectional profiles of adjacent orbits touch but do not overlap when aligned along a central X axis. With constant spacing between orbits the beam will leave gaps, as is most evident when aligned along the Y axis. To cover the entire area with a minimal level of exposure, the overall path would need to be made elliptical with an aspect ratio similar to profile 342 with a smaller total Y dimension than X dimension. FIG. 3C shows an example with circular cross-sectional profile 352 taking a path 351. While no gaps exist in FIG. 3C, the amount of orbits is greater (just over 4, as compared with 3.75 for FIG. 3B).

Figure 4A:
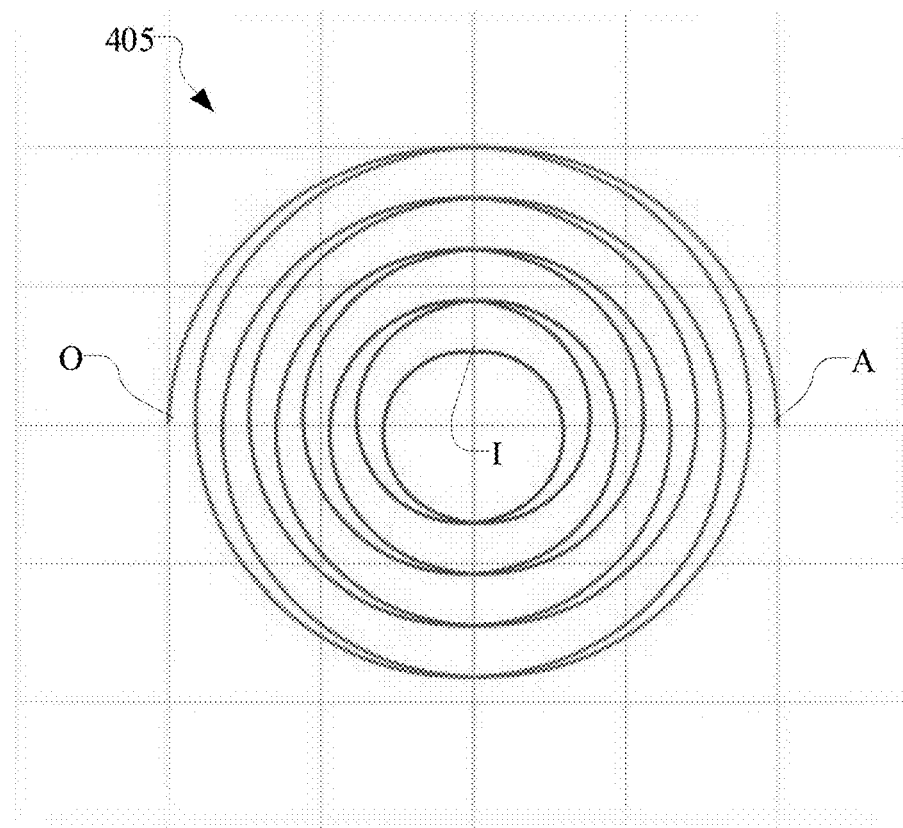
FIGS. 4A-4G are example embodiments of scanning profiles having multiple instances of a beam pattern repeated at different radial orientations.
Figure 4B:
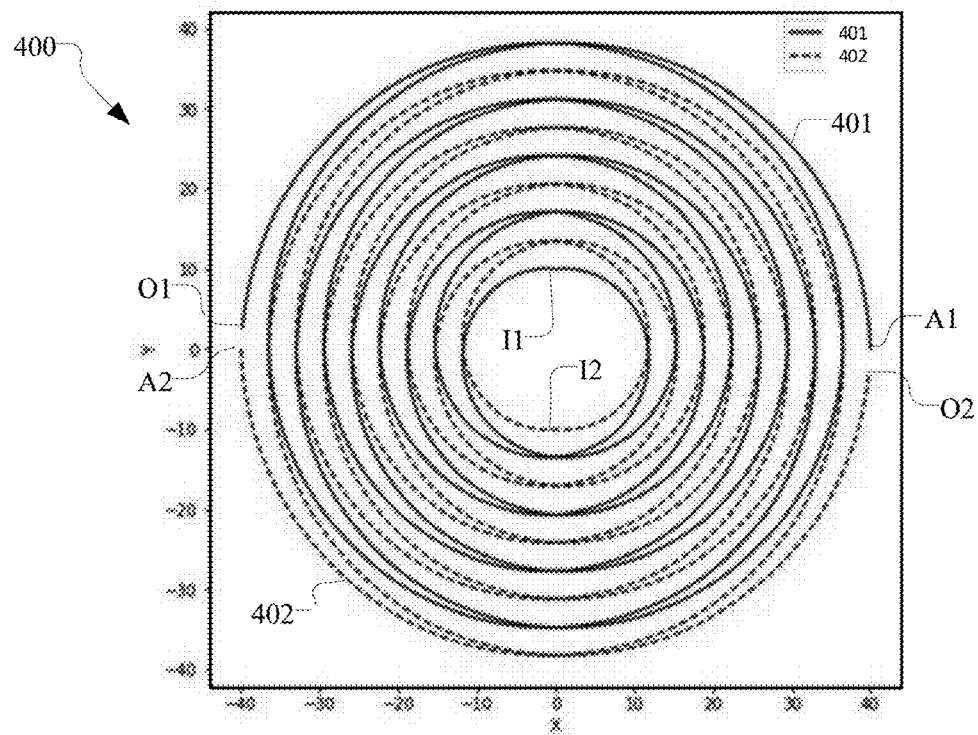

FIGS. 4A-4B are schematic views depicting an example embodiment of a scanning (or raster) profile 400 formed by a cycle 405 scanned multiple times at different radial orientations to form a group of radially shifted instances of the cycle. In this embodiment each instance of cycle 405 has the same pattern and a stopping location that differs from that instance of cycle 405's starting location. FIG. 4A depicts a cycle 405 formed by a beam path 406 where starting position A and stopping position O are in different locations that, in this example, are offset by 180 degrees. Cycle 405 is rotatable or clockable for repetition at different radial orientations to form a closed loop.

Scanning profile 400 is depicted in FIG. 4B. Here, scanning profile 400 includes two instances of cycle 405 with a difference of 180 degrees in radial orientation between them. The first instance of cycle 405 is shown by path 401, which is depicted with starting location A1, midpoint I1, and stopping location O1 in the same positions as in FIG. 4A. The second instance of cycle 405 is shown by path 402, which has starting location A2, midpoint I2, and stopping location O2. Path 402 has the same shape as path 401 but has been rotated (or clocked) by 180 degrees. For example, clocking forward can be implemented by evenly advancing the transformed theta coordinate over the A1 to O1 cycle, such that O1 ends 180 degrees off A1. Every location on path 401 is radially offset from that same or corresponding position on the next path 402 in the sequence by the same radial amount. Each of locations A2, I2, and O2 are shown in positions 180 degrees from A1, I1, and O1, respectively. In this and the other embodiments described herein, the clocking of cycles can be performed in a CW or CCW direction.

The stopping location of a first cycle (e.g., O1) is at or adjacent to the starting location of the immediately subsequent shifted cycle (e.g., A2), such that the beam can move in uninterrupted fashion from instance of cycle 405 to the next. The starting location A1 of the first cycle (e.g., path 401) and the stopping location O2 of the last cycle of the group (e.g., path 402) is substantially the same or adjacent to each other. Thus, the profile formed by the group of two or more radially shifted cycles has the same (or adjacent) starting and stopping locations, and forms a closed loop. A group of two or more cycles each having the same pattern, where each cycle has a starting location and a stopping location at the same distance (or radius) from a central point, and each cycle is rotatable in orientation such that adjacent cycles can be concatenated together to form a closed loop for the group, is referred to herein as a super cycle. Scanning the target 196 can involve moving the beam through a first cycle at a first radial orientation (e.g., path 401), then moving the beam through the same cycle at least one more time (e.g., path 402) but with the subsequent cycle at a radial orientation different from that of the first cycle. This process repeats until the super cycle is completed, at which time the process of scanning repeats itself. The scanning process can be continuously repeated until the overall procedure, e.g., the BNCT treatment, is complete.

The terms radial orientation, radial shift, and radial offset are used herein to describe a cycle that, as a whole, can be rotated (or clocked) about a central point without changing the cycle's fundamental shape. For example, in FIG. 4A, cycle 405 has a first radial orientation indicated by path 401. Cycle 405 is then radially (circumferentially) shifted by 180 degrees to the second radial orientation indicated by path 402. The radial offset between the two instances 401, 402 of cycle 405 is 180 degrees. The characterization can be similarly expressed by substituting the term azimuthal for radial (e.g., azimuthal orientation, azimuthal shift, and azimuthal offset). For example, a value of theta can define a position of an azimuth about a central point on the scannable surface (similar the hour hand of a clock, where an azimuth at a three o'clock position corresponds to a theta of 90 degrees, at six o'clock is a theta of 180 degrees, at nine o'clock is a theta of 270 degrees, etc.), and positions of cycles can be expressed with reference to theta and the azimuth.

Figure 4C:
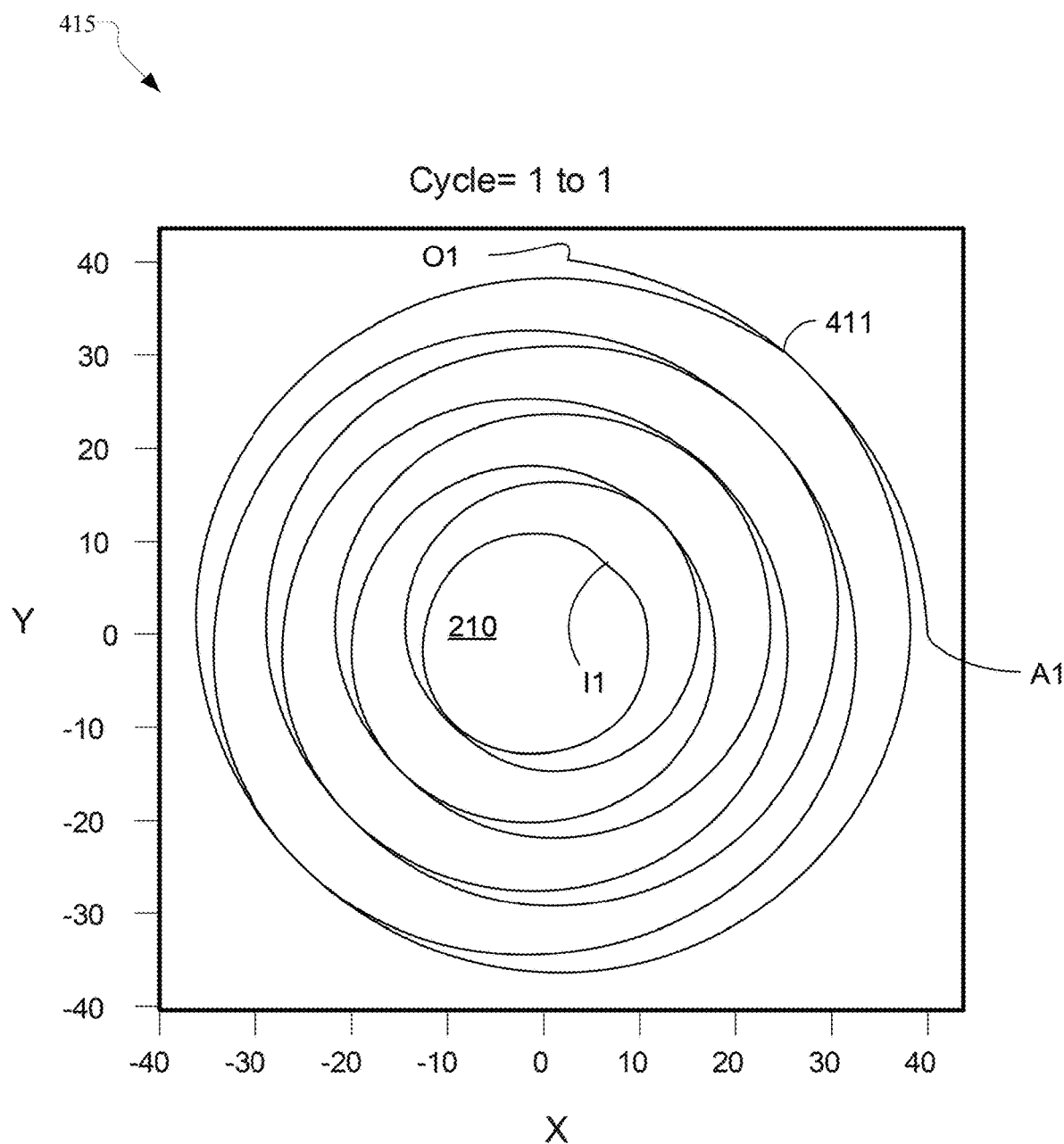
Figure 4D:
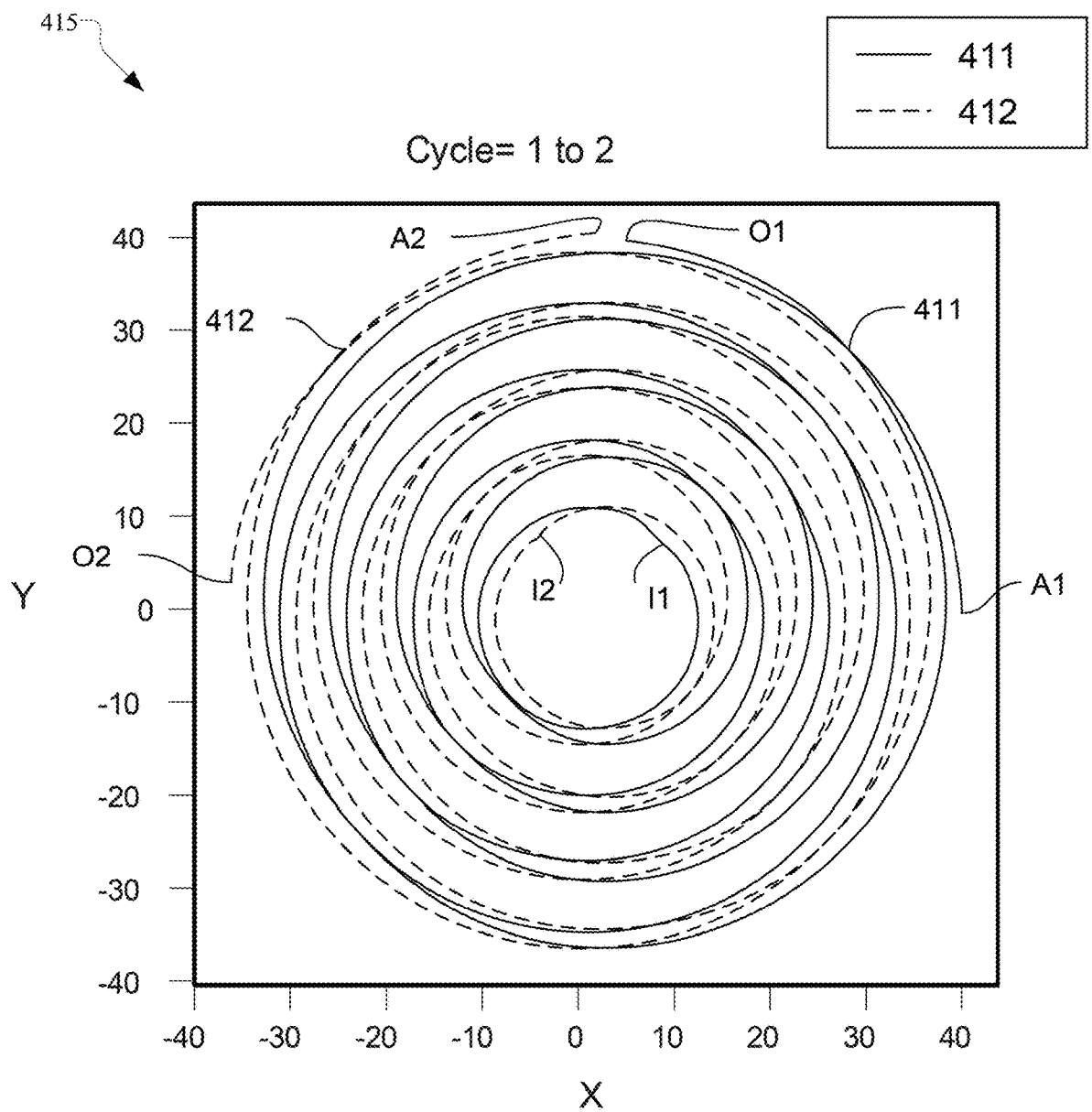
Figure 4E:
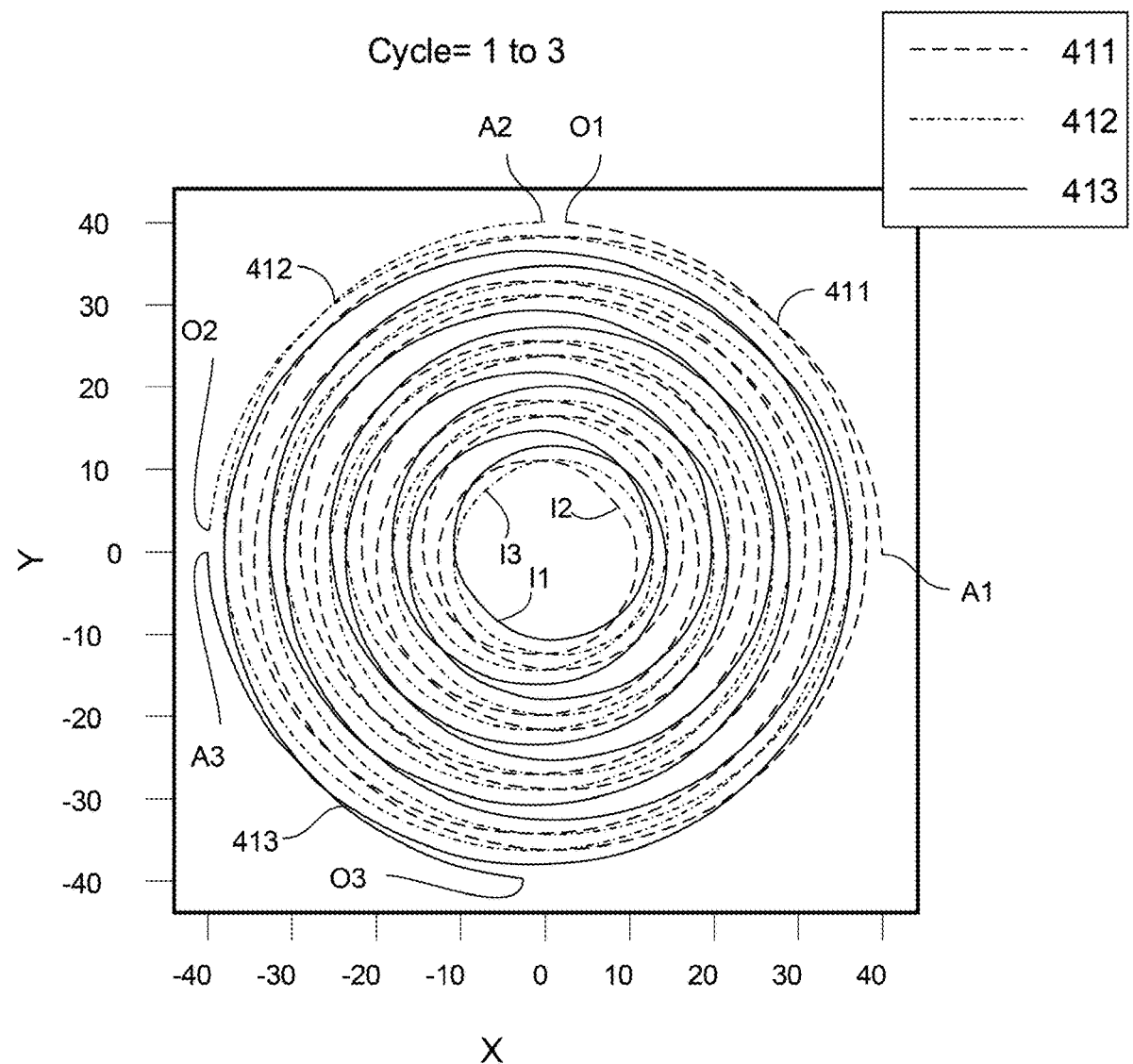
Figure 4F:
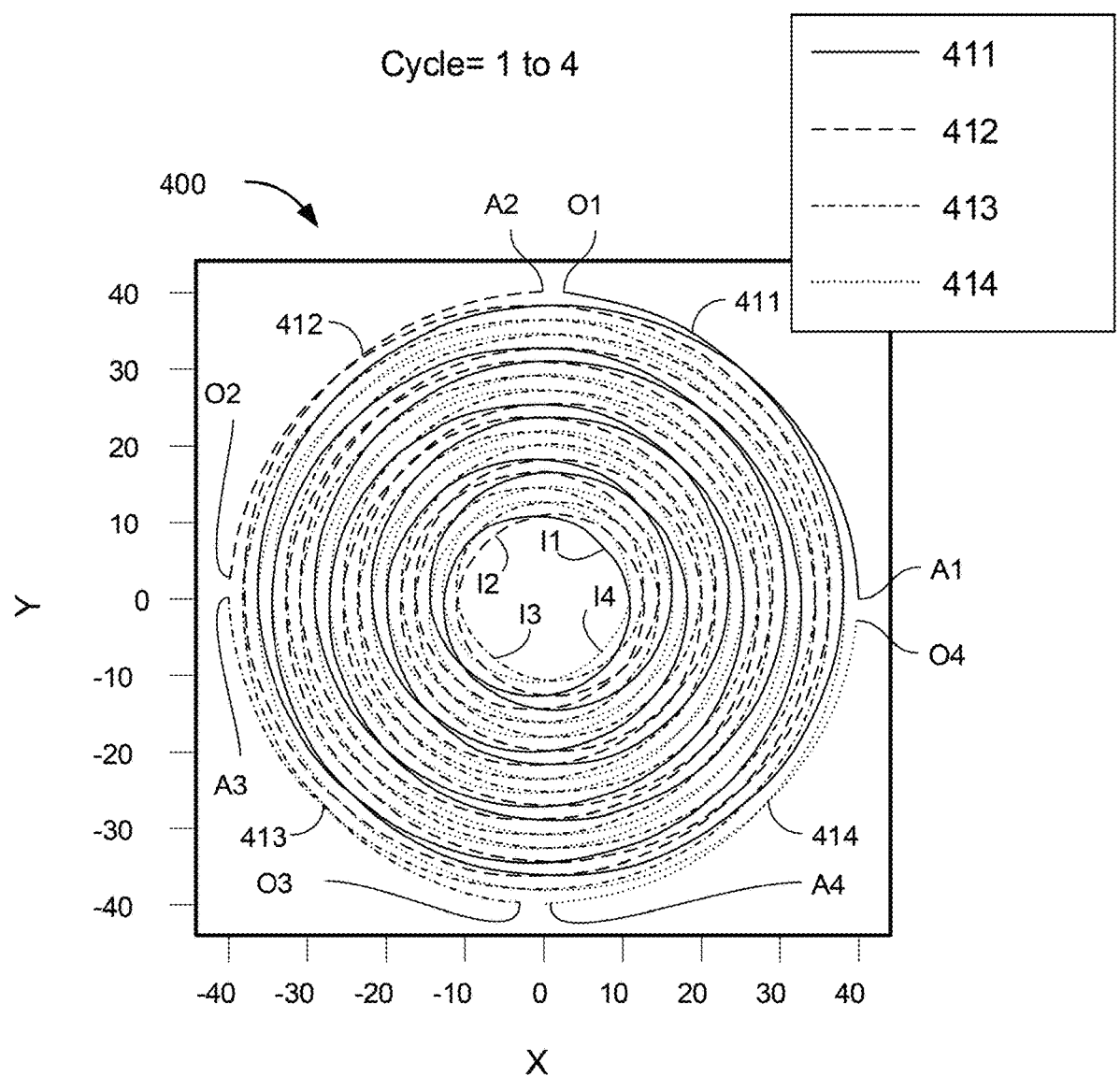

FIGS. 4C and 4D are schematic views depicting a cycle 415 that is repeated four times with a difference of 90 degrees in radial orientation between adjacent instances to form another example of scanning profile 400. In FIG. 4C, cycle 415 is formed by a beam path 411 which starts at location A1 and proceeds in CCW fashion to midpoint I1 in the inner region of surface 210, and then back to the outer region at stopping location O1. Stopping location O1 is radially offset CCW from starting location A1 by 90 degrees, which is the same amount of radial offset that is present between the cycles 415 of this profile 400. FIG. 4D depicts a second instance of cycle 415 indicated by path 412 having starting location A2, midpoint I2, and stopping location O2. FIG. 4E is the same as FIG. 4D but with a third instance of cycle 415 added as indicated by path 413 having starting location A3, midpoint I3, and stopping location O3. FIG. 4F is the same as FIG. 4E but with a fourth instance of cycle 415 added as indicated by path 414 having starting location A4, midpoint I4, and stopping location O4, to form the completed super cycle of scanning profile 400. When this embodiment of scanning profile 400 is used, the beam is transitioned through path 411, then path 412, then path 413, and then path 414 to complete the super cycle, and this super cycle can then be repeated continuously throughout the entire procedure.

Figure 4G:
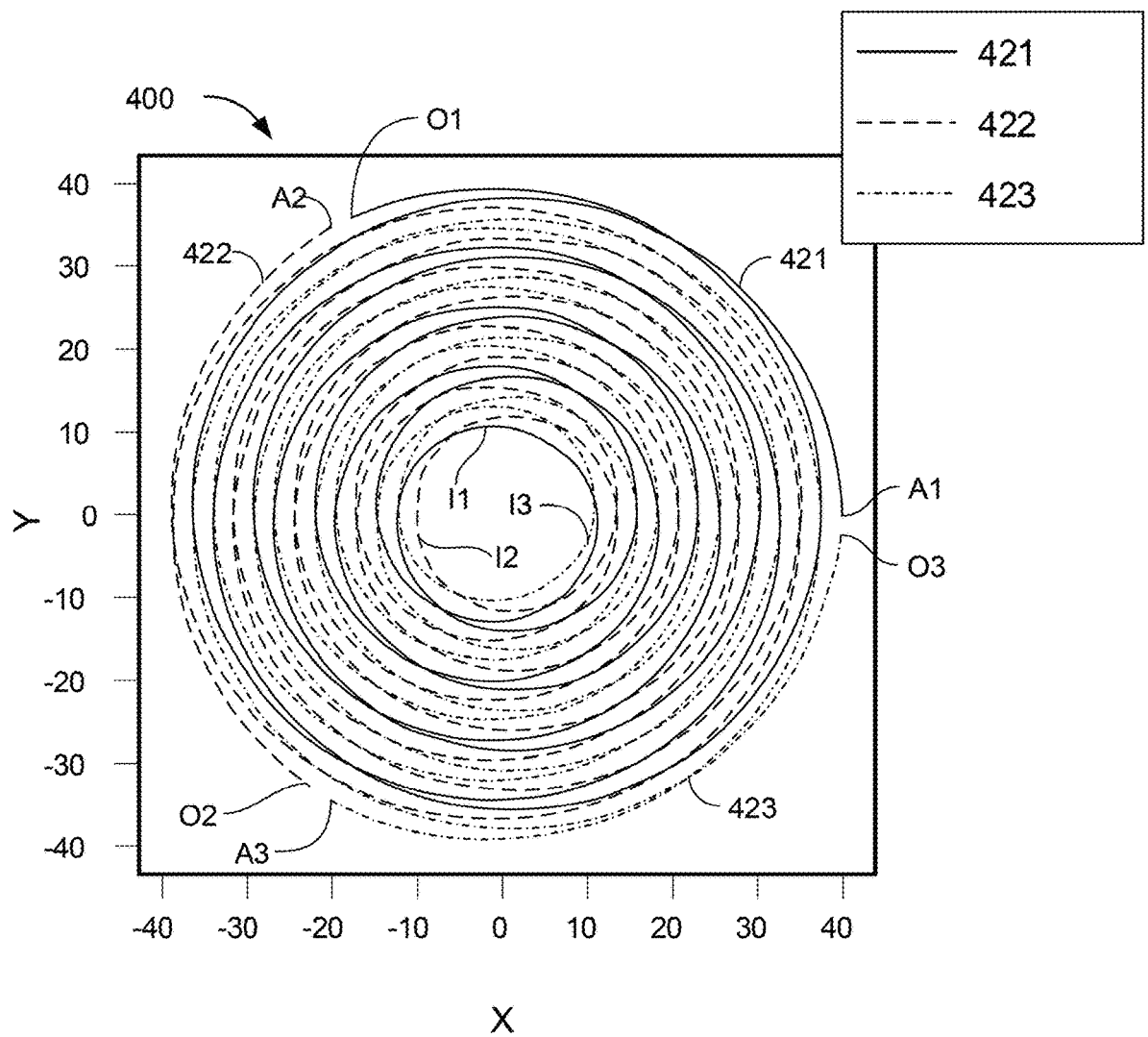

In the example illustrated by FIG. 4G, the scanning profile 400 is a super cycle including three instances 421, 422, 423 of the same cycle but with a difference of 120 degrees in radial orientation between adjacent ones. The cycle of FIG. 4G is modified from that of FIG. 4A to permit three iterations with one closed loop. The second instance 422 is radially shifted CCW by 120 degrees from first instance 421, and third instance 423 is radially shifted CCW by 120 degrees from instance 422 (radially shifted CCW by 240 degrees from instance 421). Each of locations A2, I2, and O2 are shown in positions 120 degrees CCW from A1, I1, and O1, respectively, and each of locations A3, I3, and O3 are shown in positions 120 degrees CCW from A2, I2, and O5, respectively. The beam is transitioned through instance 421, then instance 422, and then instance 423 to complete the super cycle. The super cycle can be repeated continuously multiple times throughout the entire procedure.

Additional example embodiments of scanning profile 400 can also be implemented. The amount of radial offset between the repeated patterns 301 can be determined by dividing 360 degrees by the number of pattern instances. For example, a profile 400 having five instances of a cycle can have a radial offset of 72 degrees between adjacent cycles, a profile 400 having six instances of a cycle can have a radial offset of 60 degrees between adjacent cycles, a profile 400 having seven instances of a cycle can have a radial offset of approximately 51.4 degrees between adjacent cycles, a profile 400 having eight instances of a cycle can have a radial offset of 45 degrees between adjacent cycles, a profile 400 having nine instances of a cycle can have a radial offset of 40 degrees between adjacent cycles, a profile 400 having 10 instances of a cycle can have a radial offset of 36 degrees between adjacent cycles, a profile 400 having eleven instances of a cycle can have a radial offset of approximately 32.7 degrees between adjacent cycles, a profile 400 having twelve instances of a cycle can have a radial offset of 30 degrees between adjacent cycles, and so forth.

In some implementations the stopping location of a first instance of the cycle may not be the same as, or even close to, the starting location of the next instance of the cycle. For example, the beam can bridge the gap in a relatively rapid fashion that has negligible effect on the overall thermal performance and particle loading. If the beam is pulsed, the radial shift can occur in between pulses while the beam is off.

While the embodiments described herein are shown with the same cycle repeated multiple times within a super cycle, it is noted that the cycle pattern need not be identical and differ only in radial orientation. In practice small variations will inherently be present given margins of error within the system and variances of operating conditions during the procedure. Indeed the scope of the present subject matter covers embodiments where the repeated cycle patterns are not identical, but are rather substantially the same with differences engendered by margins of error, operating condition variances, and even programmed or otherwise intended non-identicalities in the patterns.

In general, the thermal impact of a beam on the target can be investigated computationally using a computational model. Computational modelling can allow for selection of beam raster profiles that improve uniformity of particle loading on a target and/or can allow selection of raster profile that reduces (e.g., minimizes) peak transient temperature of the target. The raster profile can be characterized by a beam path and a beam profile (e.g., circular or elliptical beam with a particular dimension), as described with reference to FIGS. 8 and 9. In some implementations, the raster profile can define a beam scanning velocity.

The computational model can allow investigation of the effect on a target of varying one or more of several beam parameters, such as the beam's size and shape. Furthermore, the beam's thermal impact can be evaluated by calculating one or more figures of merit (e.g., peak temperature, temperature change, average temperature) and applying a numerical analysis to the figure of merit can allow the computational model to be used to optimize the beam's raster profile.

Figure 5A:
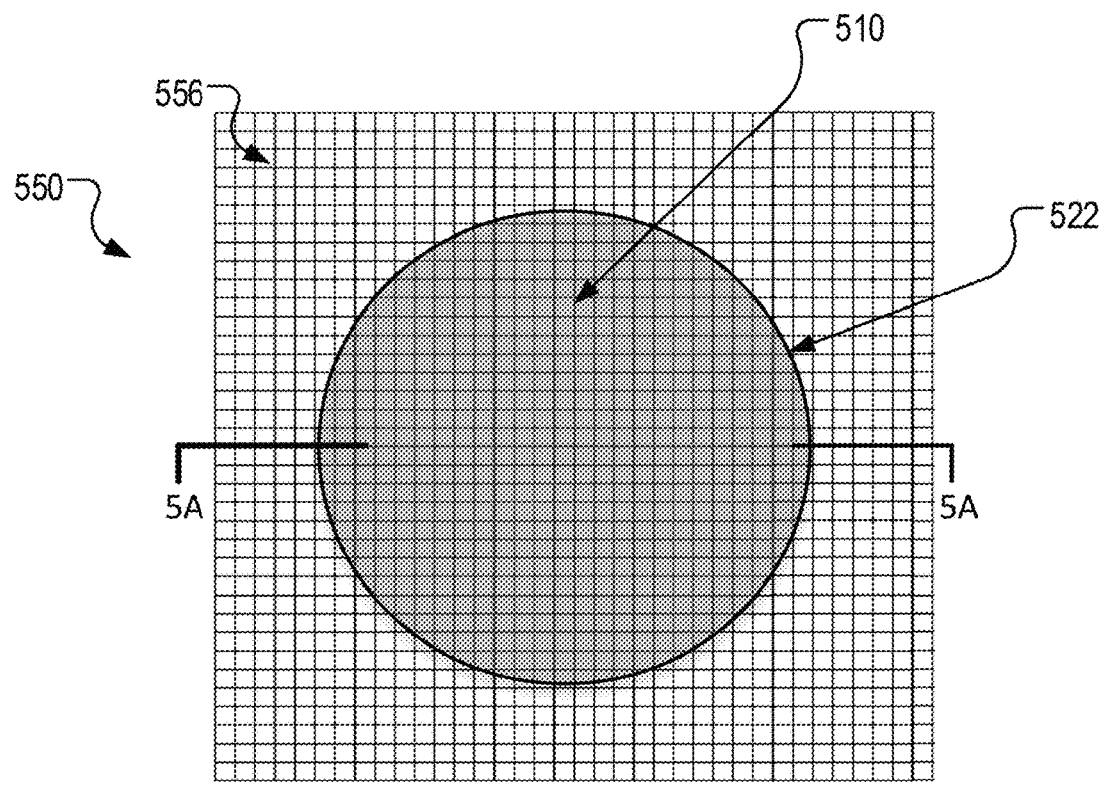
FIGS. 5A and 5B are examples of computer models including a target in accordance with the present disclosure.
Figure 5B:
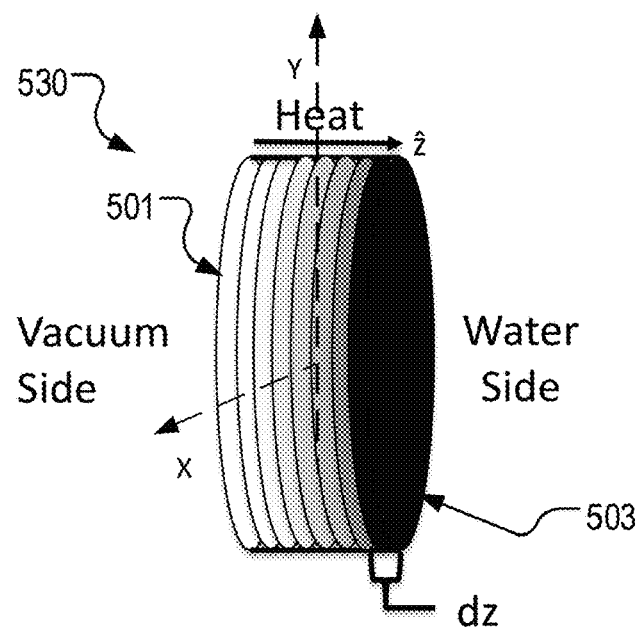

Generally, the computational model can involve generating a meshed space encompassing the target. The computational model is illustrated in FIGS. 5A and 5B, which illustrate a mesh composed of a three-dimensional grid in which the heating (temperature map) of target 196 can be modeled. The temperature values are modeled by solving a one-dimensional heat transport equation at each "pixel" (e.g., each x-y square of the grid shown in 5A). The one-dimensional heat transport equation ($u_t = c^2 u_{xx}$, defining the temperature in a pixel using the constant c as the thermal diffusivity) is solved for thermal transport through the depth of the pixel, in Z direction, as shown in 5B. Cross talk between pixels or lateral heat conduction between pixels is assumed to be negligible, such that heat only moves horizontally in Z direction, allowing the 1D approach to be used. The beam is considered to generate a propagation of heat for a particular depth into each pixel (e.g., approximately 25% of the beam energy is deposited evenly through the lithium layer and the remaining energy is deposited into the first element of the copper), corresponding to the incident beam. Compositional changes are accounted for through the depth of the pixel. Any suitable computational approach to solving the one-dimensional heat transport differential equation can be used. For example, numerical approaches can include finite-element and finite-difference approaches. For either of the finite-element and finite-difference techniques, the target 196 can be represented in a plan view 220 as a portion of a grid 226 (as illustrated in FIG. 5A). The size of the grid can vary and can be selected based on the size of the target, the beam size, and the desired computational efficiency and result accuracy. Generally, a smaller size can give more accurate answers but at computational cost. In the current example shown in FIG. 5A, the grid 226 includes 36×36 pixels (cells), but generally, the number of pixels can be within the range $10^3$-$10^5$ or more.

Generally, the grid can have the same unit cell size in each dimension or the size in each dimension can differ. Resolution can be selected to provide the ability to model beams of different size and structure in line to the physical capabilities of the system under study.

FIG. 5B is an example of a model of a target side view 230 of the target 196 illustrated in FIG. 2A. The model of the target side view 220 includes multiple layers that can correspond to the layers 201, 202, 203 described with reference to FIGS. 1B and 2C. In some implementations, the layers can have a thickness defined by the pixels of the numerical grid 226. In some implementations, a boundary of the target layer 201 is modeled as corresponding to vacuum and a boundary of the target substrate 203 is modeled as corresponding to a coolant fluid (e.g. water), defining the boundary conditions of the one-dimensional heat transport equation.

Figure 6A:
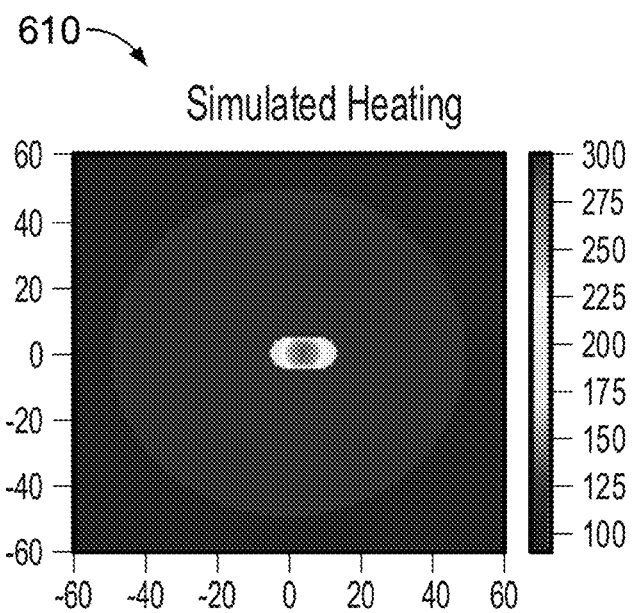
FIGS. 6A-6D are examples of modeled thermal maps in accordance with the present disclosure.
Figure 6B:
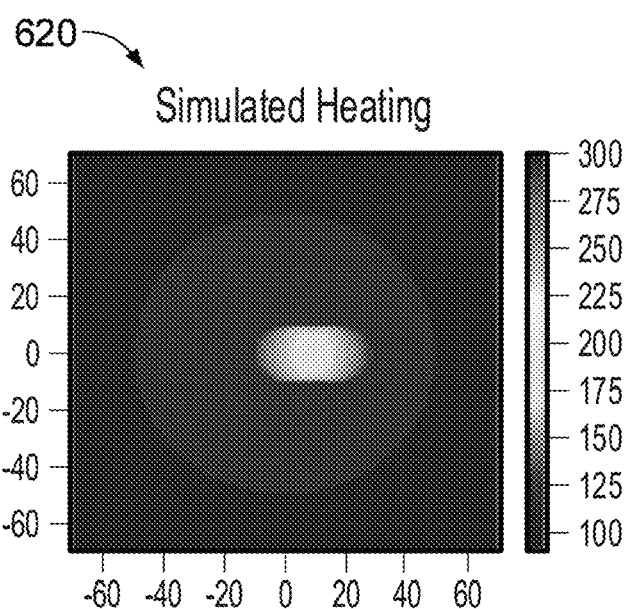
Figure 6C:
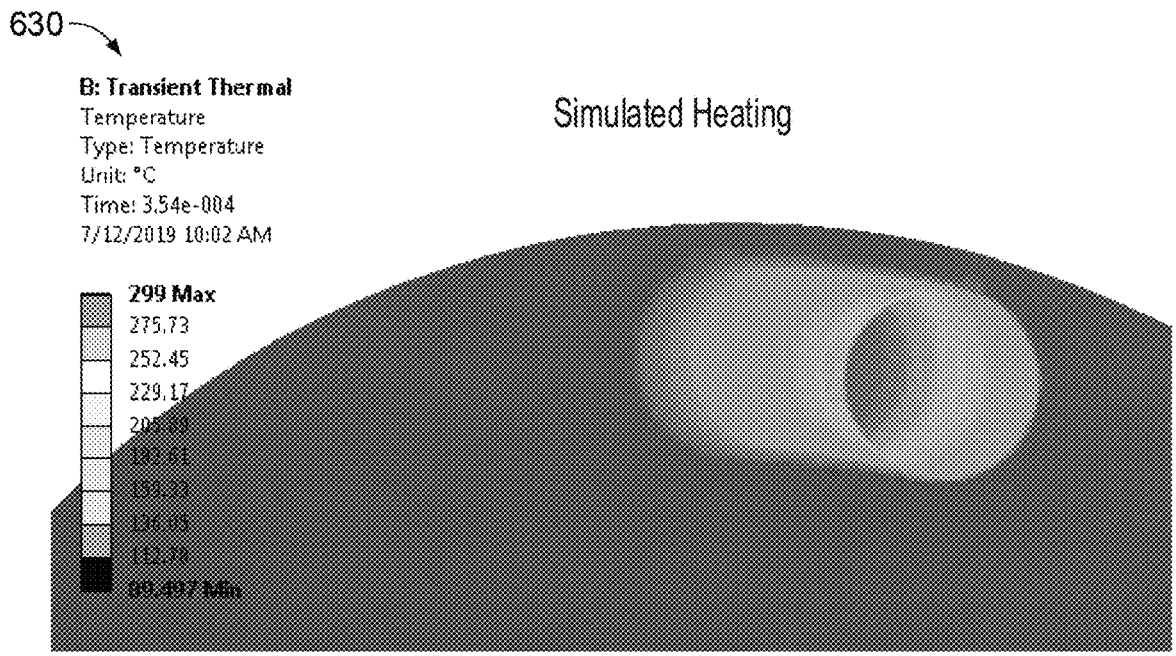
Figure 6D:
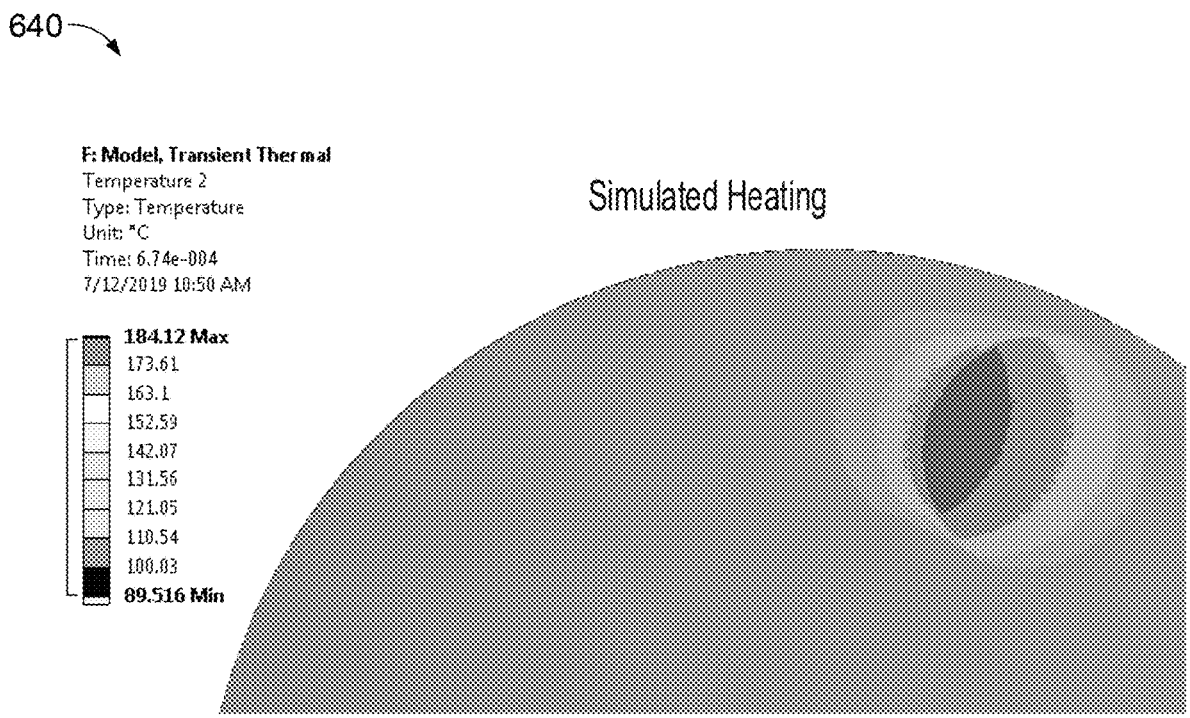

FIGS. 6A-6D show examples of simulated thermal maps using the model described with reference to FIGS. 5A and 5B. FIGS. 6A and 6B show examples of simulated thermal maps 610, 620 determined using the computational model as described above for 10 mm and 20 mm beam sizes, respectively. FIGS. 6C and 6D show examples of simulated thermal maps 630, 640 determined using an ANSYS® engineering simulation software for 10 mm and 20 mm beam sizes, respectively. The model used to generate the simulated thermal maps 610, 620 is based on a transient code that tracks the surface particle loading based on any given beam profile in combination with any raster profile. The model was benchmarked against a transient model calculated with a three-dimensional heat transfer code ANSYS® as validation.

The overall profile of the simulated thermal maps 610, 620, 630, 640 calculated based on assumption of a scanning frequency of 120 Hz generally matches for both 10 mm and 20 mm beam sizes. For example, FIGS. 6A and 6C both show a surface temperature distribution with a distinctive heat maximum corresponding to the center of the 10 mm proton beam. The highest average lithium surface temperature was 284° C. as determined by the model and 299° C. as determined by the ANSYS® model. The temperature drop from the center of the 10 mm proton beam to the margins of the 10 mm proton beam registered 162.7° C. as determined by the model and 177.7° C. as determined by the ANSYS® model. FIGS. 6B and 6D both show a dispersed surface temperature distribution corresponding to the 20 mm proton beam. The highest average lithium surface temperature was 177° C. as determined by the model and 184° C. as determined by the ANSYS® model. The temperature drop from the center of the 20 mm proton beam to the margins of the 20 mm proton beam registered 55.7° C. as determined by the model and 63.3° C. as determined by the ANSYS® model The fact that some of the calculated temperature values are above the acceptance limit for Lithium shall not undermine the validity of the model.

Table 1 shows heating map simulation results that enable a comparison between the predicted temperature variation ($\Delta T$) and peak temperature ($T_{max}$) as determined using the model described with reference to FIGS. 5A and 5B and using an ANSYS® engineering simulation software. The data was generally analyzed to determine the correlation between the modeled values with respect to the values determined using the computationally expensive ANSYS® engineering simulation software to determine the reliability of the developed model. The reliability of the model is reflected by the differences in the thermal results. A temperature rise difference of about 10% was found between the two sets of results, indicating agreement between the model and the transient ANSYS® model.

TABLE 1

|  | Model (10 mm) | ANSYS (10 mm) | % Diff (10 mm) | Model (20 mm) | ANSYS (20 mm) | % Diff |
|---|---|---|---|---|---|---|
| ΔT | 162.7° C. | 177.7° C. | 8.44% | 55.7° C. | 63.3° C. | 12.01% |
| $T_{max}$ | 284° C. | 299° C. | 5.02% | 177° C. | 184.6° C. | 4.11% |

As is evident from the raster patterns shown in FIGS. 3A-5G, there are numerous points in each pattern where the beam path crosses itself. Each crossing point is a location where the target surface is exposed to a significantly higher particle flux (e.g., double) than locations where the target surface is exposed just a single time for each super cycle. Where the time between consecutive passes over a crossing point is relatively long, and heat from the first pass can be sufficiently dissipated before the second exposure, the increased dose associated with the second exposure may not result in excessive heating at the crossing point. However, where a crossing point is exposed twice in a relatively short period, these crossing points can be locations of unacceptably high thermal loads. Accordingly, in some implementations, the computational models described above can be used to reduce thermal load on a target by determining paths that reduce the number of crossing points that experience multiple passes of the beam in quick succession.

For example, a computational model can be used to vary parameters of a raster profile to avoid crossing the beam path recently traversed within a threshold time period below which excessive heating of that target location may occur. FIGS. 7A-7F are schematic views depicting examples of raster patterns that are instructive in demonstrating such recent path avoidance (RPA) strategies. In some implementations, the RPA pattern can be determined based on an iterative process. The iterative process can start with a trochoid shape, defined as an (x(t), y(t)) position for a given time (t). For radii, $r_1$, $r_2$ and frequencies $\omega_1$, $\omega_2$, the basic trochoid follows the following equations over time t:

$x(t) = r_1 \cos(\omega_1 \cdot t) + r_2 \cos(\omega_2 \cdot t)$ $y(t) = r_1 \sin(\omega_1 \cdot t) + r_2 \sin(\omega_2 \cdot t)$.

For an L-lobed trochoid with outer radius, $r_{max}$, and inner radius, $r_{min}$, the values for the radii and frequencies are:

$r_1 = (r_{max} + r_{min})/2$ $r_2 = (r_{max} - r_{min})/2$ $\omega_1 = L+1$ $\omega_2 = 1$ A radius with a maximum radius value $r_{max}$ substantially equal to the beam width and a minimum radius value $r_{min}$ substantially equal to half the beam width can provide good results for a uniform-intensity beam. Optimal values for $r_{max}$ and $r_{min}$ can be found through optimization algorithms and a heat simulation code.

Setting t to be time dictates the speed at which the raster moves, which can be varied based on capabilities of the steering magnets and a target burning risk. For example, a high raster speed may exceed the capability of the steering magnets or a low raster speed may lead to burning of the target (if exposed too long to a particular radiation dose). For all modified trochoid raster profiles, the next beam position is calculated such that the velocity remains approximately constant. Varying the velocity based on the beam position may offer another route for improvement. The optimal velocity profile can be found by training a machine-learning algorithm on the results generated by the heat simulation code, as described with reference to FIGS. 8A, 8B, 9A, and 9B.

A constant-velocity trochoid pattern can give good results in target usage but could lead to overheating. For example, the trochoid pattern visits the center of the target with a fairly high frequency because as the trochoid path continuously follows each lobe. In order to solve the heating problem, the raster pattern can be modified such that instead of following the path along each lobe continuously, the $\omega=(L-1)^{th}$ lobe order is used. Visiting the lobes in this order gives the center additional time to cool down between lobes. This is where the name Recent Path Avoidance (RPA) raster comes from, as recently visited paths are avoided, prolonging the time it takes for the beam to cross its recent path. For some values of L, it may be optimal to take lobes more frequently than every $\omega=(L-1)^{th}$ lobe. Any lobe frequency, $\omega$ that is coprime with the total number of lobes, L, could work depending on the physical parameters of the system (beam profile, target shape, target material, etc.). The choice of lobe frequency $\omega$ can be optimized through computational techniques, such as using a machine learning algorithm.

In some implementations, the raster path includes a modification of $r_1$ and $r_2$ to create a filter that only allows the raster path to follow every $(L-1)^{th}$ lobe and otherwise to follow the $r_{max}$ value to allow the center of the target time to cool down.

For example, an initial RPA raster (RPA One) can include the following radii and frequencies:

$r_1 = -(r_{max} + r_{min}) \cdot \cos\left(\frac{L}{2 \cdot (L-1)} \cdot t\right)^E$ $r_2 = r_{max}$ $\omega_1 = L+1$ $\omega_2 = 1$ The exponent E can be greater than 10 and smaller than 1000 (10<E<1000). The exact value of the exponent E can depend on multiple factors. For example, E can be set to be large enough to give a well-defined window for the filter to avoid having the raster oscillate around the perimeter, which may cause the beam to miss the target. E has to be set smaller than a threshold value that defines a very small window that would cause the lobes to become too narrow, overheating the target. In some implementations, E can be set such that E=100·(L−3) with L being greater than or equal to 4 and smaller than or equal to 8 (4≤L≤8).

RPA-One works well for minimizing heating, but can leave a region of the target underutilized. RPA-One can be used to develop RPA-Two, which adds another term to $r_1$, to define another set of L lobes that can fill in the underused region. RPA Two uses the following radii and frequencies:

$$r_1 = -(r_{max} + r_{min}) \cdot \cos\left(\frac{L \cdot t}{2L-1}\right)^E - r \cdot \cos\left(\frac{L \cdot t}{2 \cdot (2L-1)}\right)^E$$

$$r_2 = r_{max}$$

$$\omega_1 = 2L + 1$$

$$\omega_2 = 1$$

The coefficient r can be greater than $r_{min}$ and smaller than the difference between the radii limits $r_{max}$ and $r_{min}$ ($r_{min} < r < r_{max} - r_{min}$). The exponent E can be greater than 100 and smaller than 10000. The exact values of the coefficient r and exponent E can be optimized using the heat simulation and an optimization algorithm. In some implementations, one or more additional rasters (RPA-N) can be determined by adding terms to $r_1$, each new term can be optimized to minimize target heating and target usage variation.

Figure 7A:
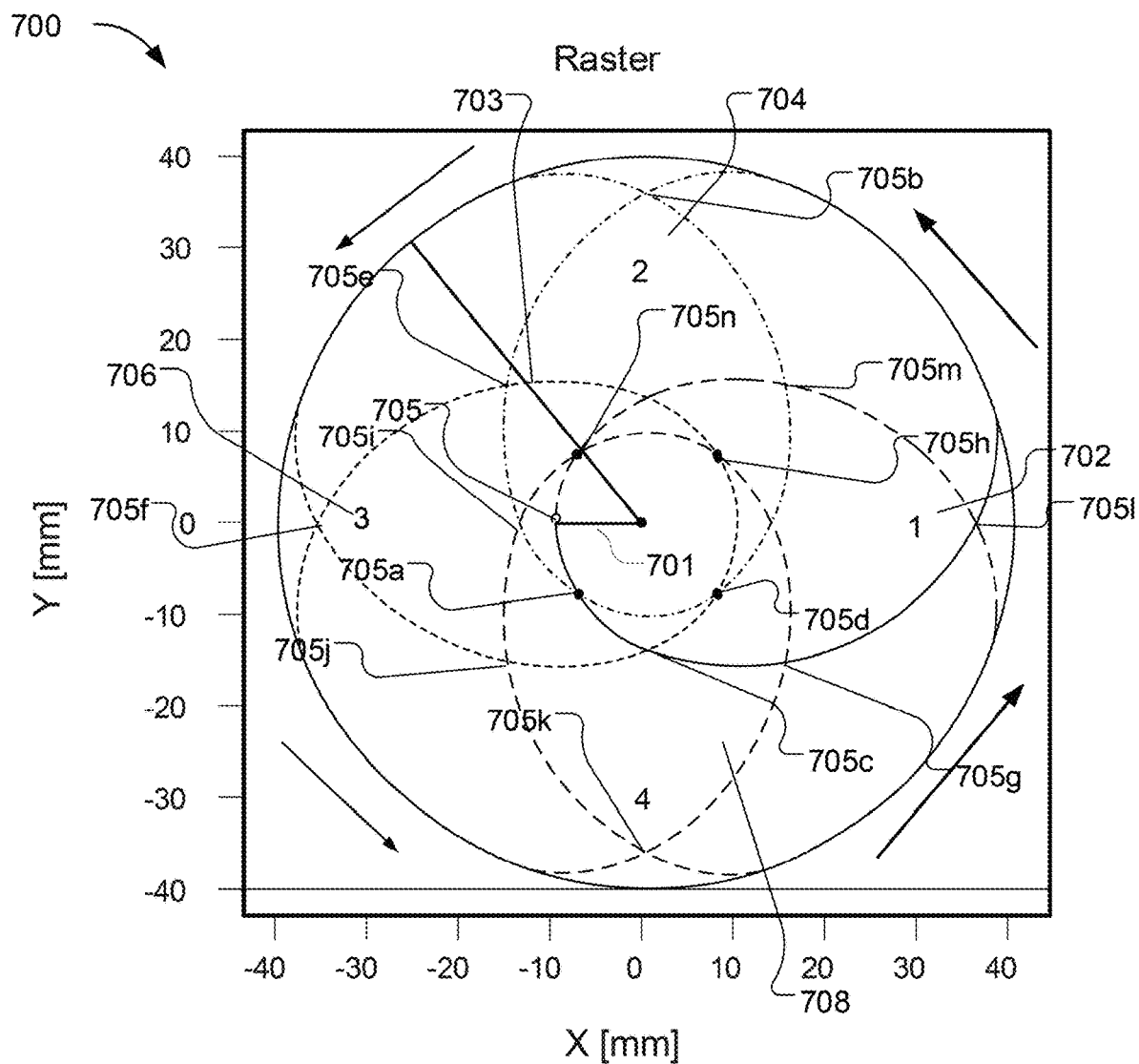
FIGS. 7A-7F are examples of recent path avoidance (RPA) patterns.

FIG. 7A illustrates an example of a trochoid raster pattern 700 that can be generated by directing the beam towards a (static or rotating) target. The trochoid raster pattern 700 can be used as an initial raster pattern for an iterative process, as described with reference to FIG. 10. The trochoid raster pattern 700 can include multiple lobes 702, 704, 706, 708 (e.g., 4 four lobes as illustrated in FIG. 7A). In some implementations, the values for the inner radius 701 and the outer radius 703 can be found through optimization algorithms and by using the heat simulation code described above with reference to FIGS. 5A and 5B. The trochoid raster pattern 700 includes multiple beam crossing points 705a, 705b, 705c, 705d, 705e, 705f, 705g, 705h, 705i, 705j, 705k, 705l, 705m, 705n where the beam path crosses itself. For example, considering the startup point 705 of the trochoid raster pattern 700, the first beam crossing point is 705a, the second beam crossing point is 705b, the third beam crossing point is 705c, the fourth crossing point is 705d, and the fifth crossing point is 705e.

Figure 7B:
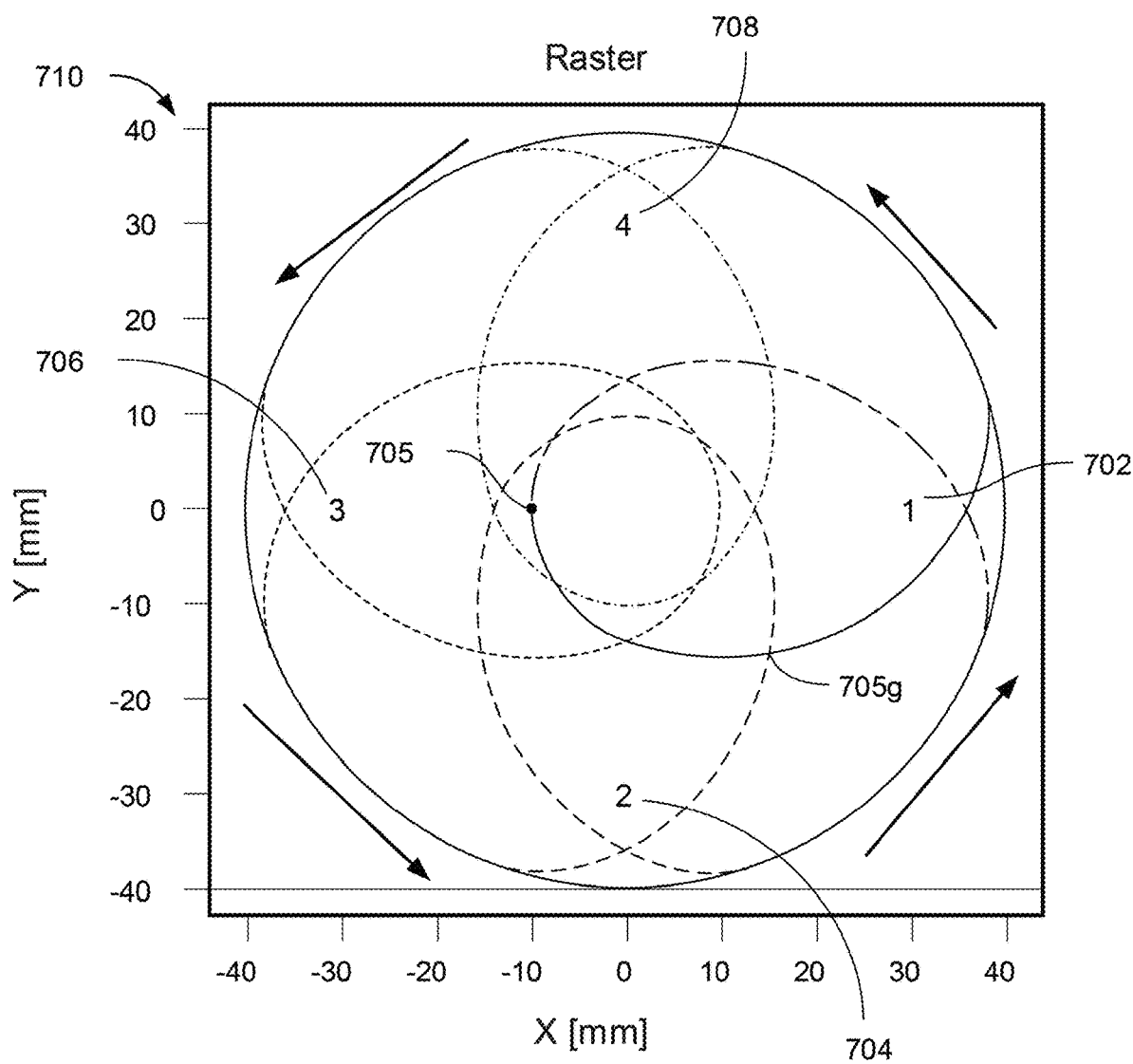

FIG. 7B illustrates an example of a modified raster pattern 710, wherein the order of the lobes 702, 708, 706, 704 is modified to extend the cooling period of the points where the beam path crosses itself, generating a recent path avoidance (RPA) pattern. The time duration between subsequent beam crossing points is directly proportional to the arc length traversed by the beam between respective consecutive crossings. For example, considering the startup point 705 of the modified raster pattern 710, the first crossing point is 705g, which is associated with a longer arc length than the arc length corresponding to the first crossing point 705a of the trochoid raster pattern 700.

In some implementations, the RPA pattern can be further modified to fill underused regions of the target, as described with reference to FIGS. 7C-7F.

Figure 7C:
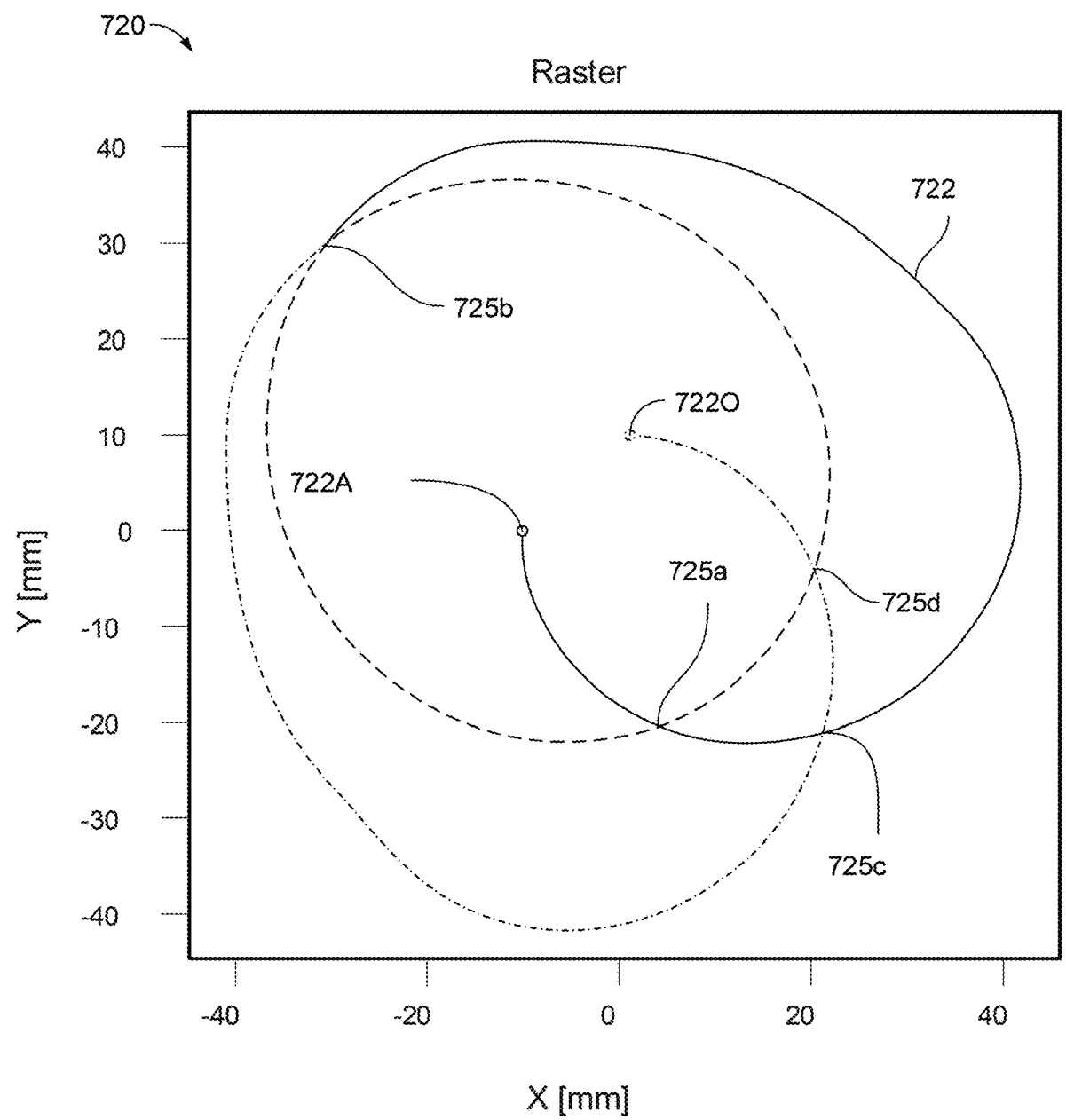

FIGS. 7C-7F are schematic views depicting examples of recent path avoidance (RPA) patterns 720 that are repeated multiple (e.g., four) times to form a full super cycle of the scanning profile. FIG. 7C illustrates the first cycle 722 of the RPA pattern. The first cycle 722 of the RPA pattern 720, starting at 722A and stopping at 722O, includes multiple beam crossing points 725a, 725b, 725c, 725d where the beam path crosses itself. For example, considering the startup point 722A of the first cycle 722 of the RPA pattern 720, the first beam crossing point is 725a, the second beam crossing point is 725b, the third beam crossing point is 725c, and the fourth crossing point is 725d.

Figure 7D:
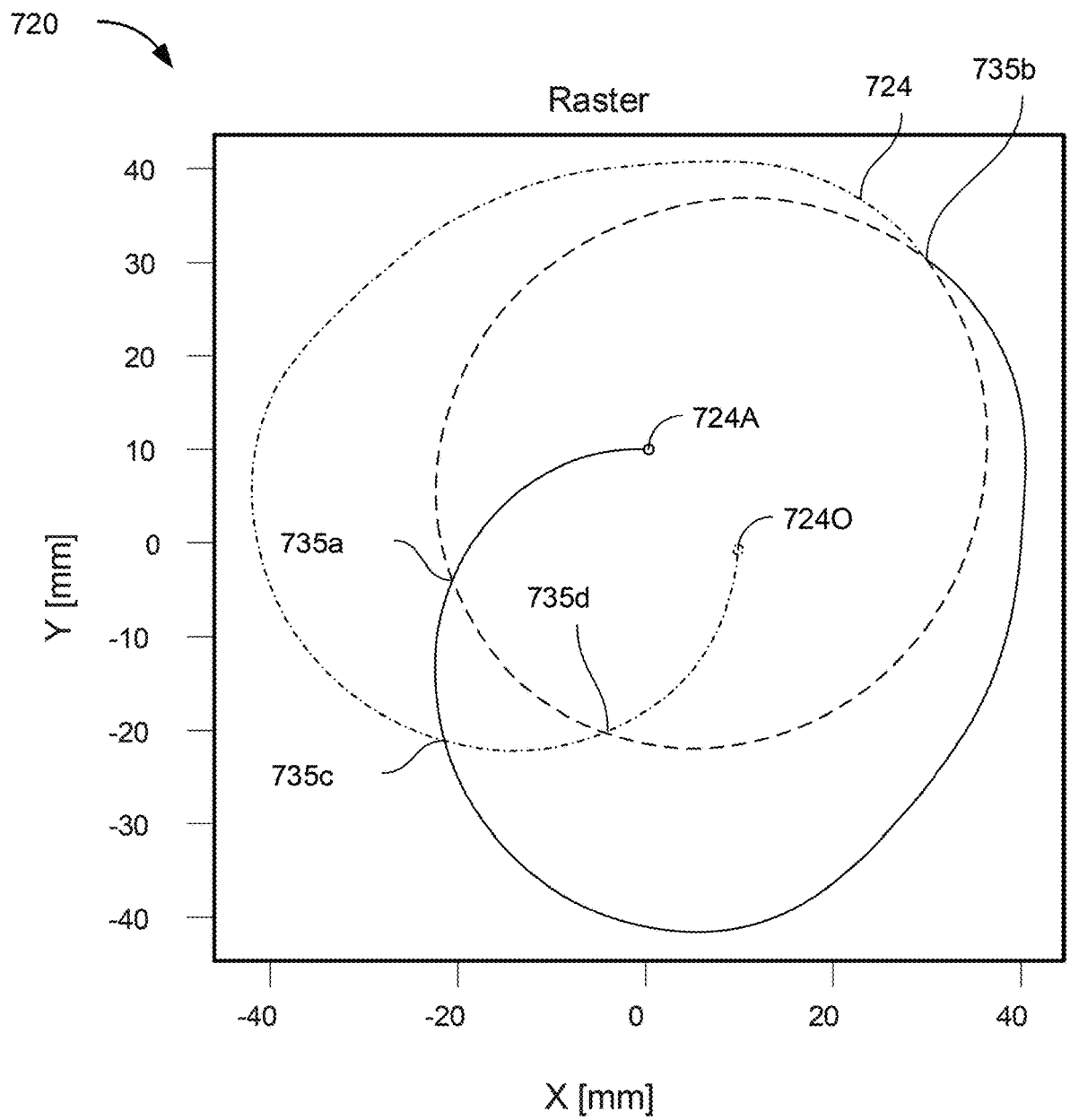

FIG. 7D illustrates the second cycle 724 of the RPA pattern 720 that can be performed after the completion of the first cycle of the RPA pattern. The second cycle 724 of the RPA pattern 720, starting at 724A and stopping at 724O, includes multiple beam crossing points 735a, 735b, 735c, 735d where the beam path crosses itself. For example, considering the startup point 724A of the second cycle 724 of the RPA pattern 720, the first beam crossing point is 735a, the second beam crossing point is 735b, the third beam crossing point is 735c, and the fourth crossing point is 735d.

Figure 7E:
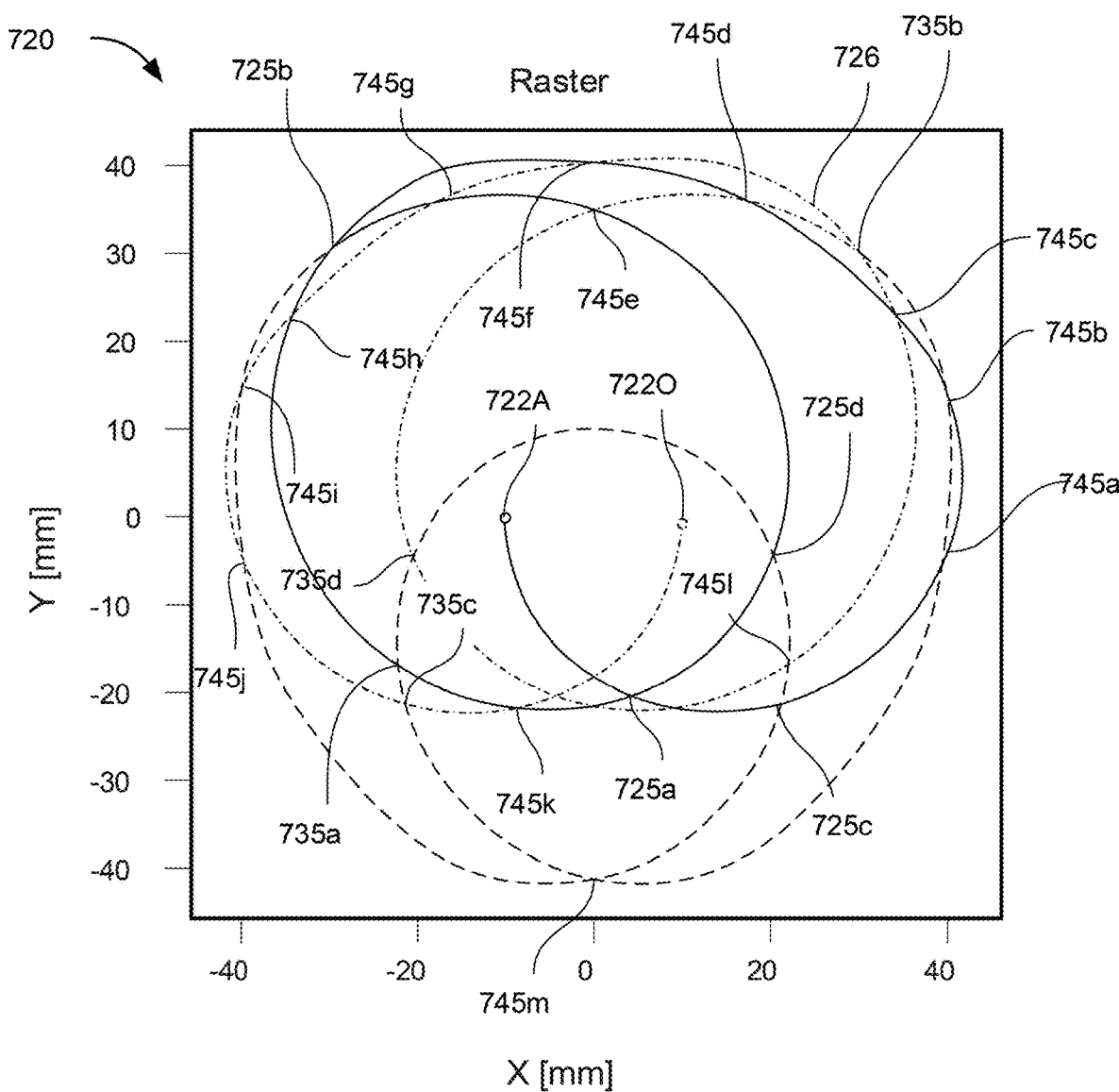

FIG. 7E illustrates the first two cycles 726 of the RPA pattern 720. The first two cycles 726 of the RPA pattern 720 include the beam crossing points 725a, 725b, 725c, 725d of the first cycle 722, the beam crossing points 735a, 735b, 735c, 735d of the second cycle 724 and beam crossing points 745a, 745b, 745c, 745d, 745e, 745f, 745g, 745h, 745i, 745j, 745k, 745l, 745m where the path of the second cycle 724 crosses the path of the first cycle 722.

Figure 7F:
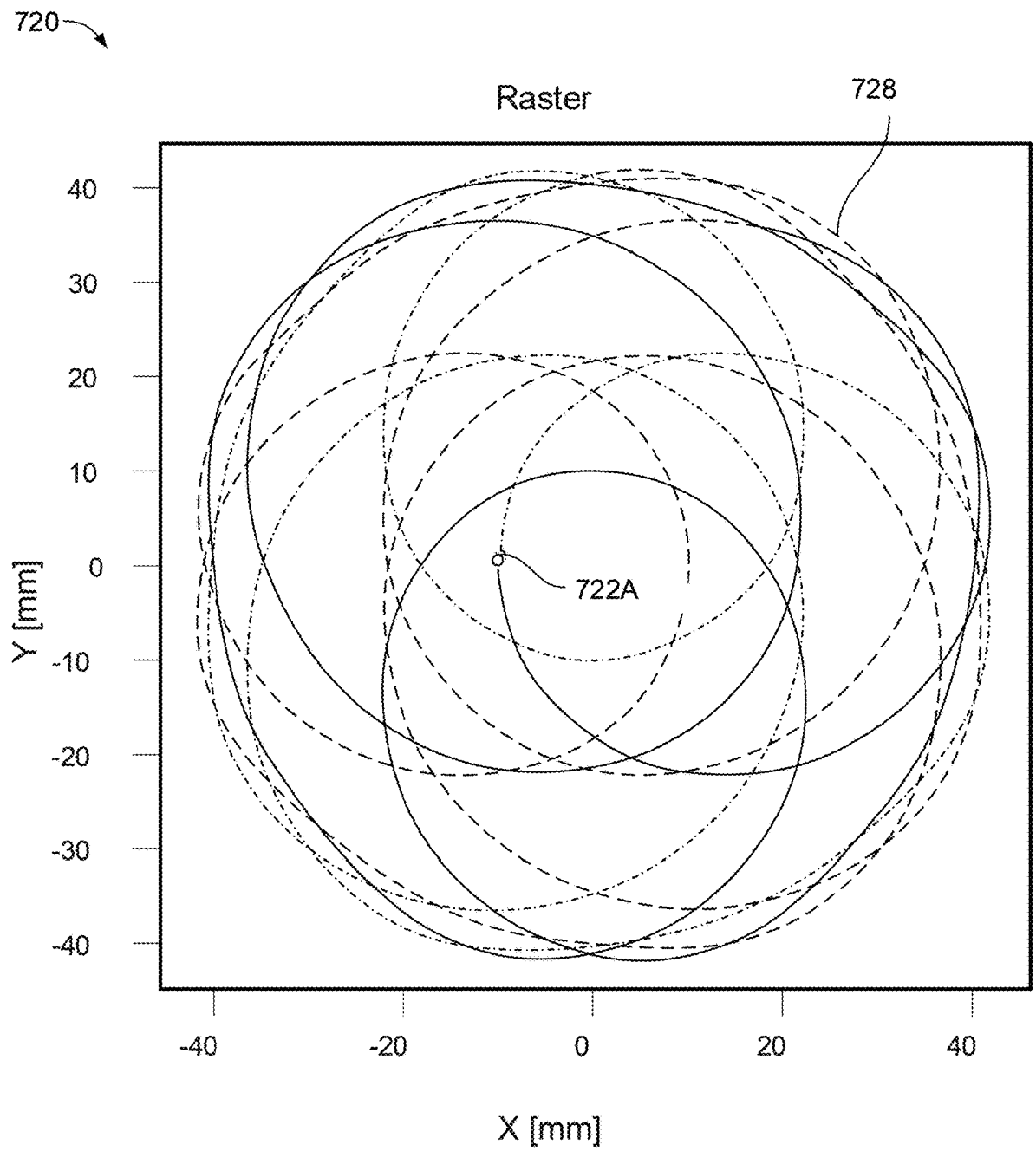

FIG. 7F illustrates the full super cycle 728 of the RPA pattern 720. The full super cycle 728 of the RPA pattern 720 includes the beam crossing points of each cycle (e.g., beam crossing points 725a, 725b, 725c, 725d of the first cycle 722, the beam crossing points 735a, 735b, 735c, 735d of the second cycle 724) and the beam crossing points where the path of one cycle intersects the path of another cycle.

Each cycle of the RPA pattern 720 includes a stopping position 722O, 724O distanced from a starting position of the corresponding cycle 722A, 724A. The stopping position of a cycle (e.g., stopping position 722O of the first cycle) corresponds to the starting position of the subsequent cycle (e.g., starting position 724A of the second cycle). As illustrated in FIG. 7F, the RPA pattern 720 is formed by beam path 728, which starts at location 722A and proceeds in CCW fashion along four cycles (including the first two cycles 726 illustrated in FIG. 7E), and then back to the starting position 722A. The example RPA pattern 720 illustrated in FIG. 7F forms a raster profile with four cycles that form a closed pattern based on a single full super cycle to close the loop.

Figure 8A:
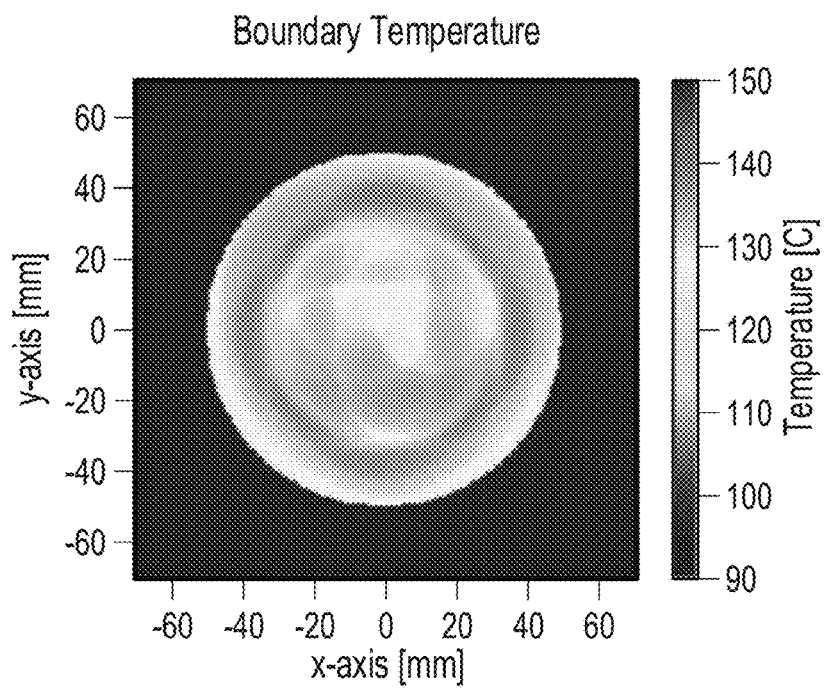
FIGS. 8A and 8B are examples of simulated boundary temperature and usage maps.
Figure 8B:
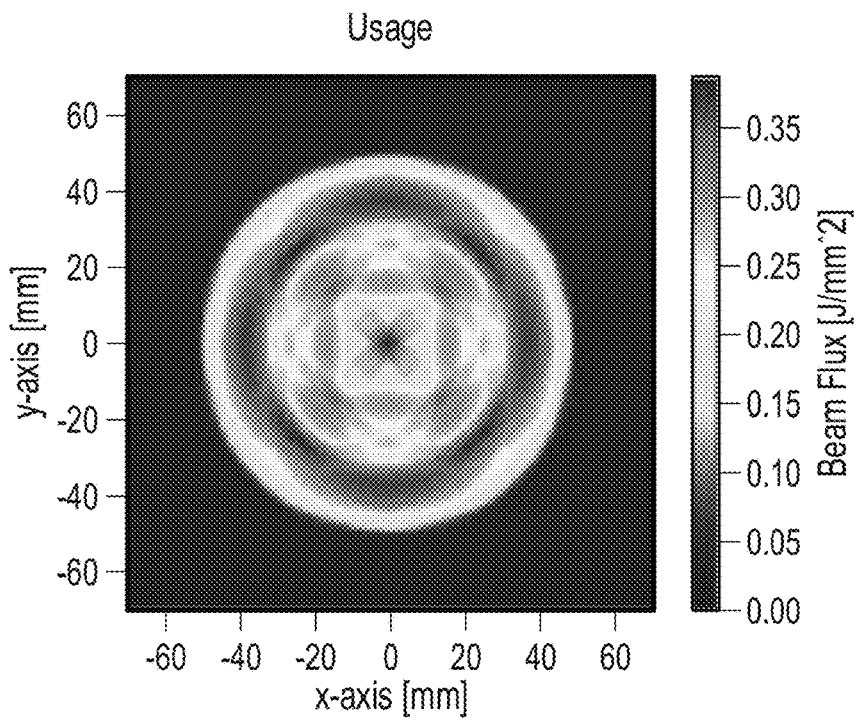

FIGS. 8A and 8B show examples of a simulated boundary temperature map 802 and a simulated target usage map 804 corresponding to target scanning using the RPA pattern described with reference to FIG. 7B, for a continuous path following the RPA pattern with constant velocity. Boundary temperature map 802 defines the boundary between lithium and copper layers of the target, considering neutronic models that identify the boundary as highest energy deposition layer with the hottest measured or modeled temperature. The target usage map 804 indicates how much lithium is consumed by each portion (pixel) of the target in response to the irradiation with the proton beam that is directed towards the target using the RPA pattern.

The simulated boundary temperature map 802, as illustrated by FIG. 8A, includes a circularly dispersed heat maxima corresponding to the most used cells, as illustrated by the simulated target usage map 804 of FIG. 8B. The highest peak temperature within the simulated boundary temperature map 802 was less than 150° C. The temperature variation across the target surface within the simulated boundary temperature map 802 was about 40° C. The simulated boundary temperature map 802 and the simulated target usage map 804 indicate that scanning the target using the using the RPA pattern is efficient in preventing target damage through blisters or bubbles.

Additional modeling using the transient code provides several figures of merit for evaluating target performance. The figures of merit include: peak temperature, temperature change, average temperature, usage efficiency, nominal frequency, and beam shape. The peak temperature includes the maximum temperature found in the target at any time. The temperature change includes maximum temperature found in the target at any time minus the initial target temperature. The average temperature is the average of the temperatures of all cells in the target. The usage efficiency includes the total target beam flux divided by the usage of the maximally used cell normalized to the total number of cells within the target. The results of the modeling using the transient code for evaluating target performance, in response to one super cycle or super cycles that are repeated multiple (e.g., 4) times, are included in Table 2.

TABLE 2

| Figure of Merit | 1 Super cycle | 4 Super cycles |
| --- | --- | --- |
| Peak Temperature | 140 | 140 |
| Temperature Change | 18.8 | 18.5 |
| Average Temperature | 133 | 133 |
| Usage Efficiency | 66.4% | 73.5% |
| Nominal OD Frequency | 240 Hz | 240 Hz |
| Beam OD/shape | 20 mm round | 20 mm round |

Figure 9A:
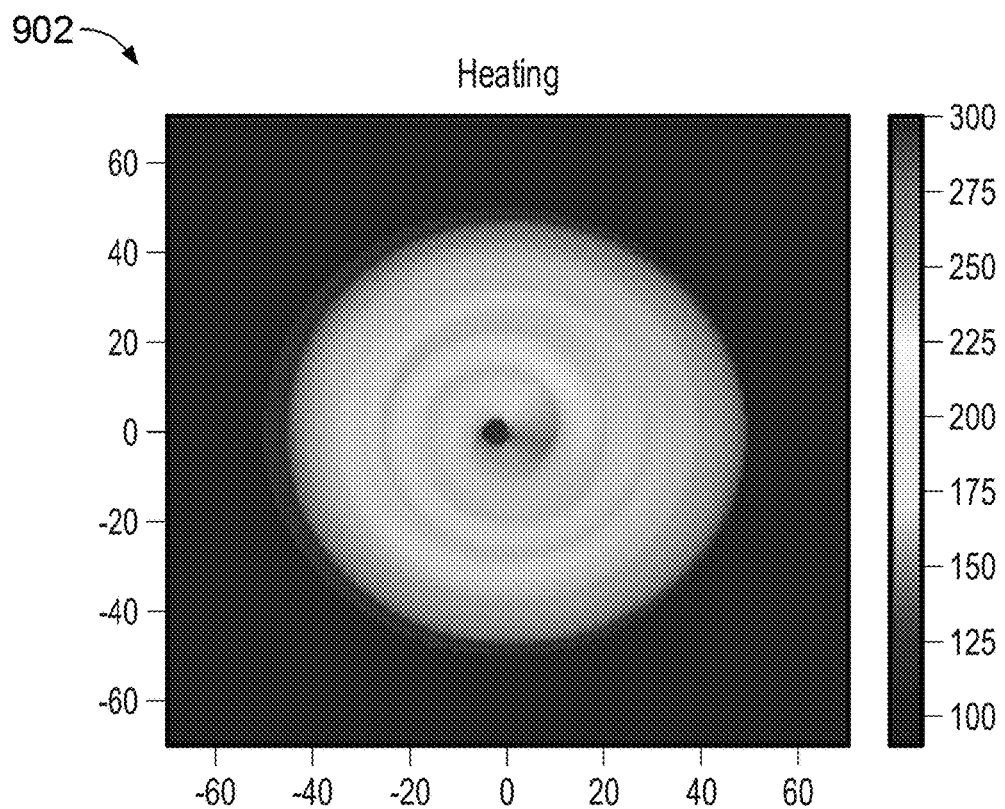
FIGS. 9A-9J are examples of simulation results in accordance with implementations of the present disclosure.
Figure 9B:
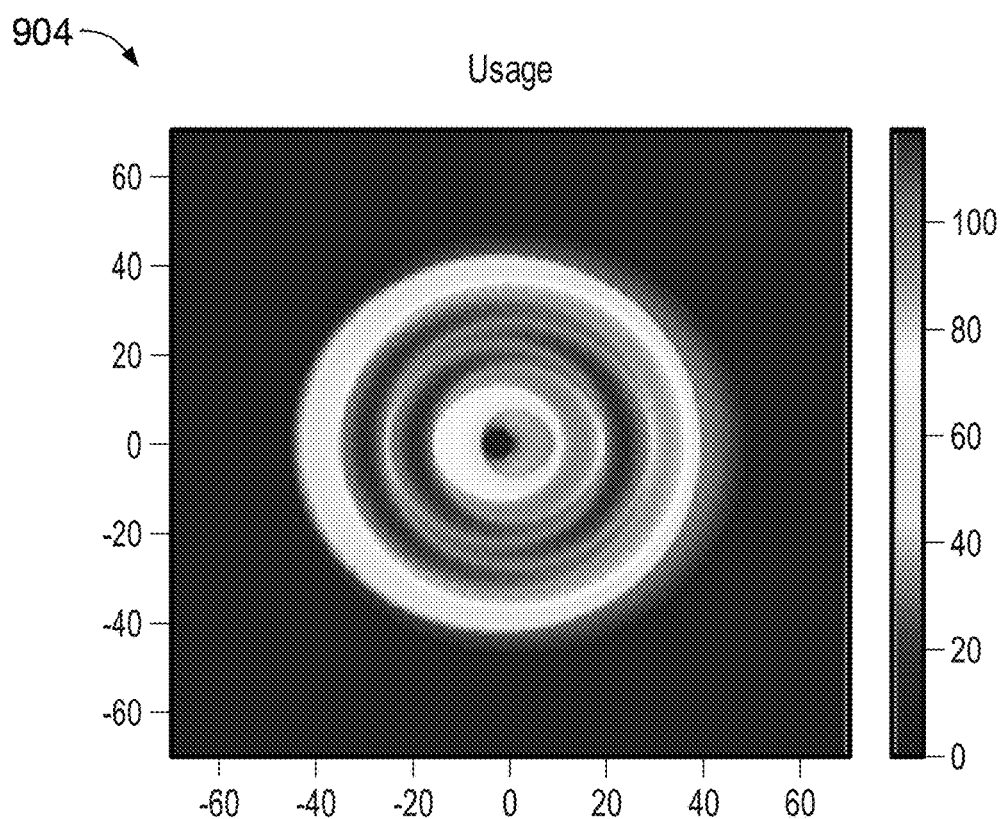
Figure 9C:
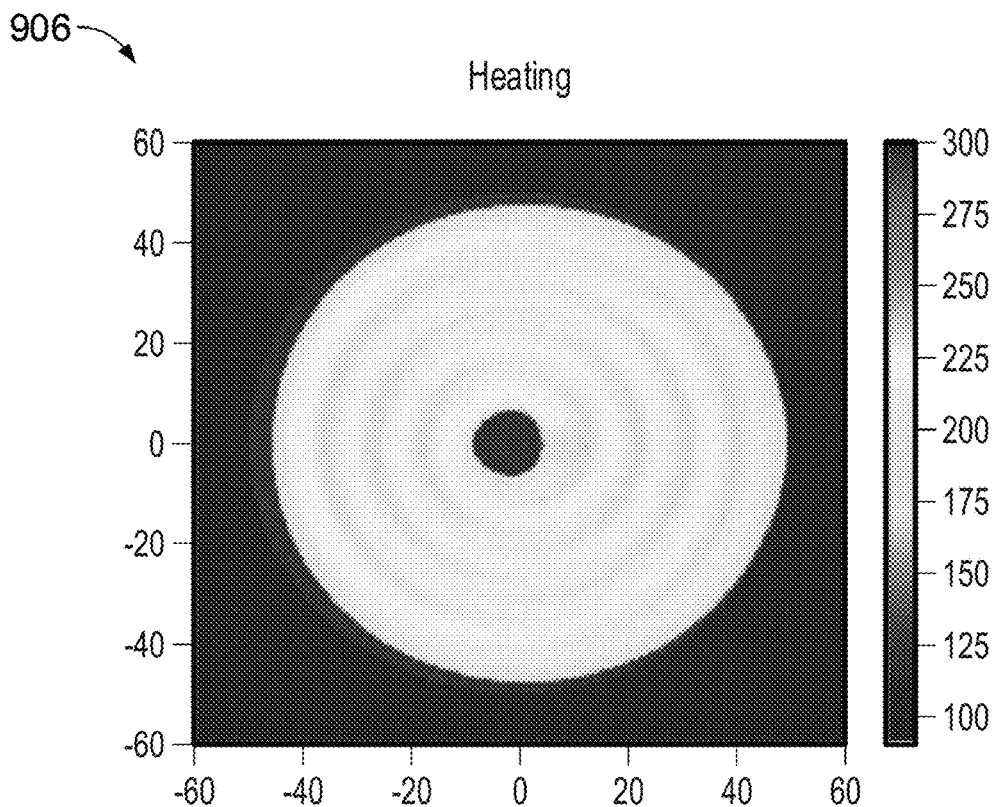
Figure 9D:
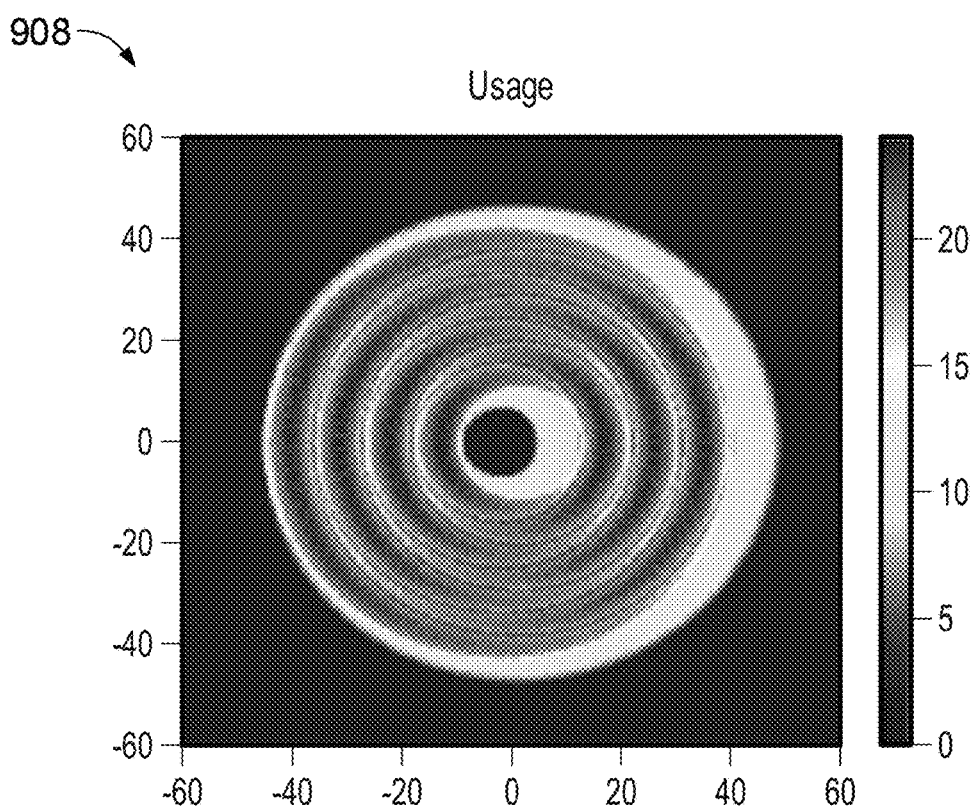
Figure 9E:
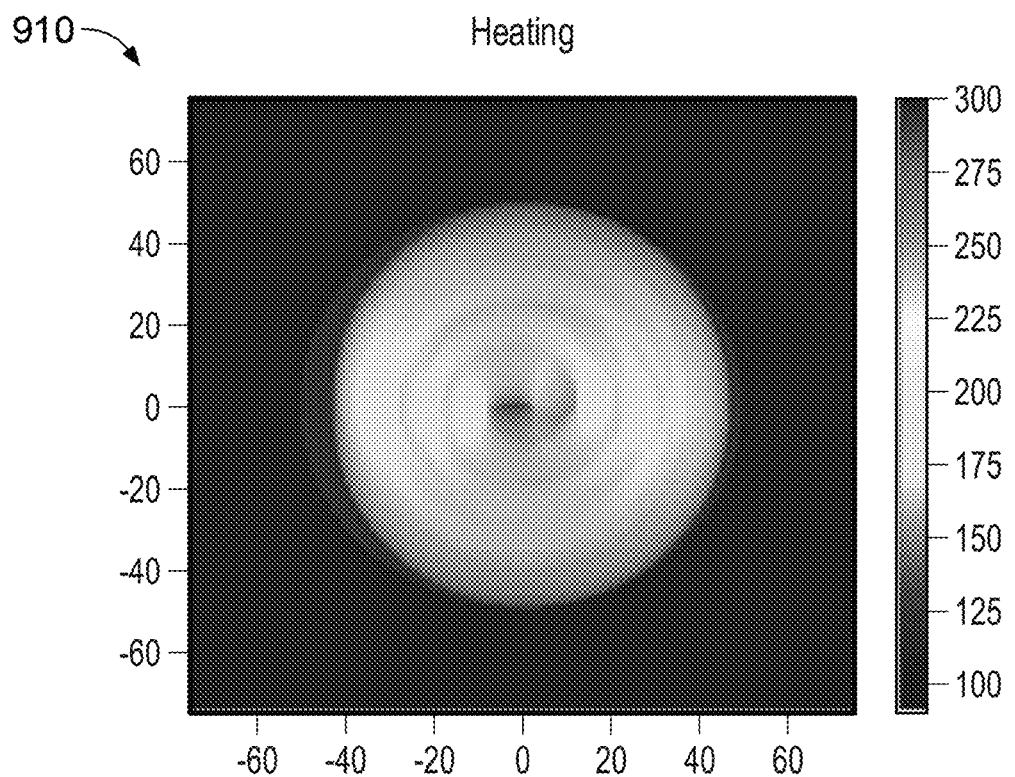
Figure 9F:
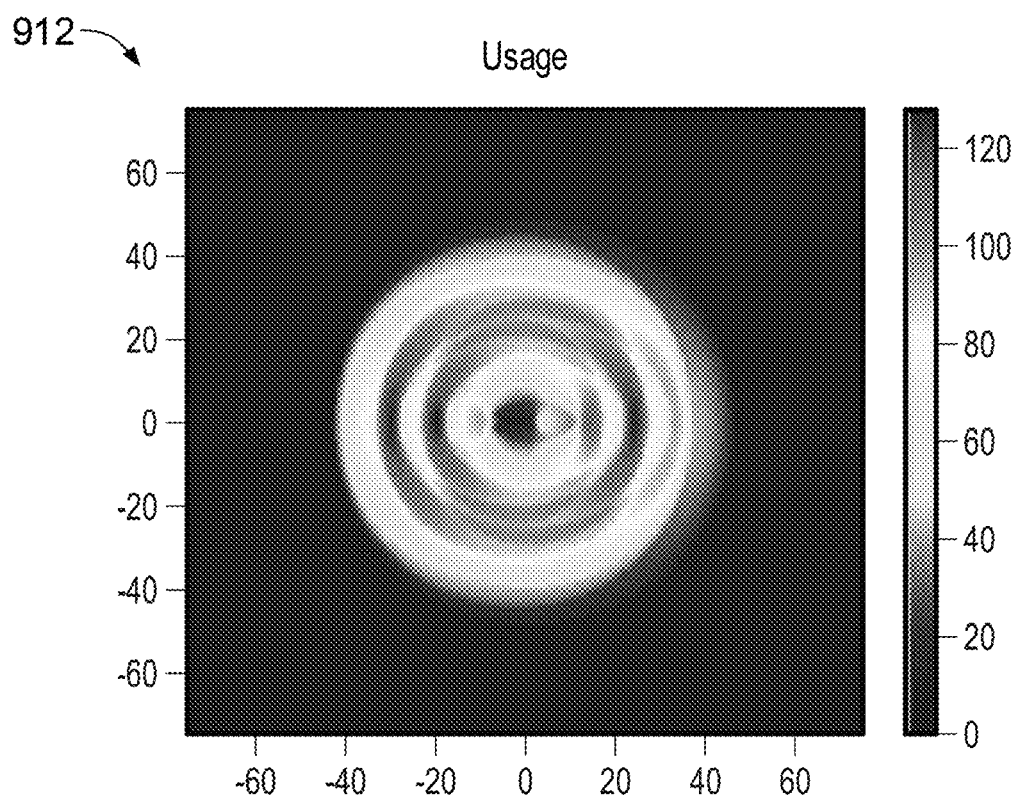
Figure 9G:
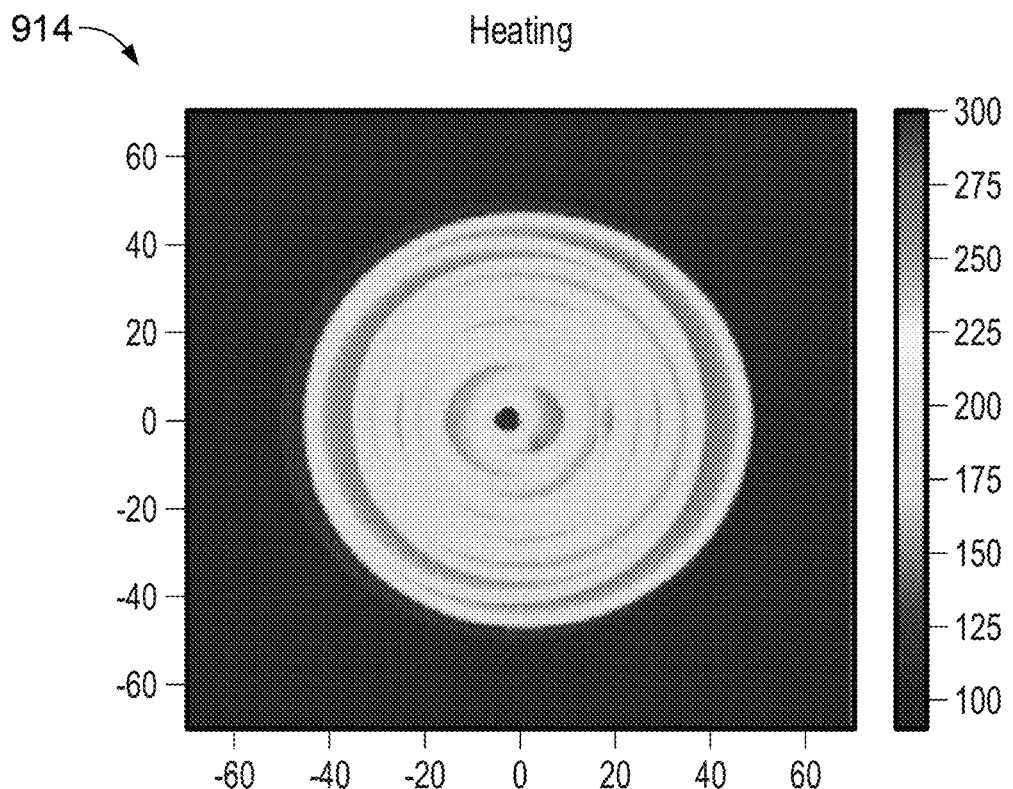
Figure 9H:
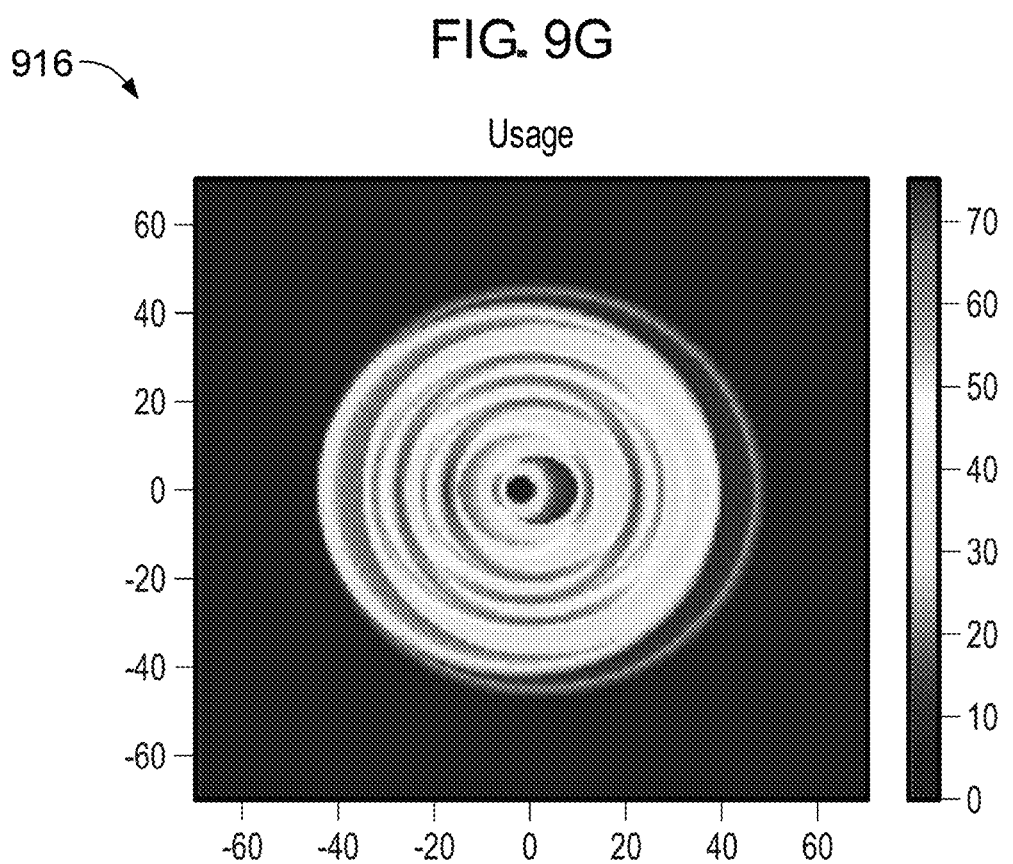
Figure 9I:
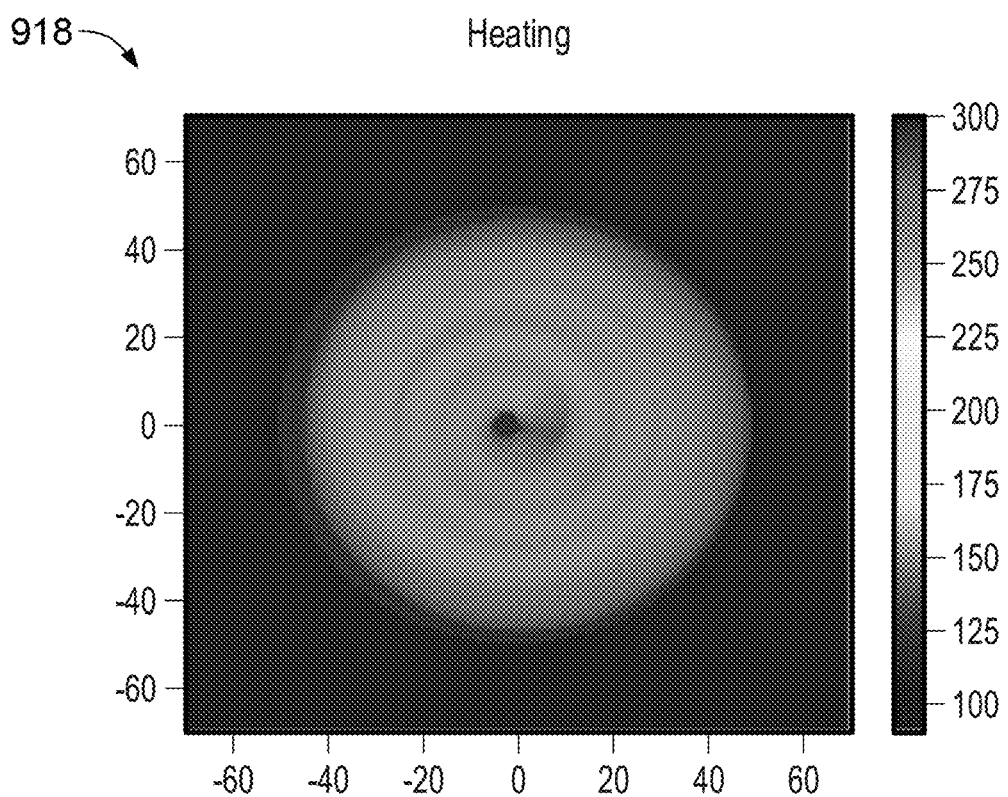

FIGS. 9A-9J show examples of simulation results for multiple beam profiles to compare target heating and target usage. Each simulation uses raster pattern 300 to highlight variation caused by the different beam profiles themselves. FIGS. 9A and 9B show the simulated thermal map 902 and the simulated usage map 904, respectively for a 20 mm circular (not hollow) beam having a frequency of 120 Hz. FIGS. 9C and 9D show the simulated thermal map 906 and the simulated usage map 908, respectively for a 10 mm circular (not hollow) beam having a frequency of 120 Hz. FIGS. 9E and 9F show the simulated thermal map 910 and the simulated usage map 912, respectively for a 15 mm by 25 mm elliptical (not hollow) beam having a frequency of 120 Hz. FIGS. 9G and 9H show the simulated thermal map 914 and the simulated usage map 916, respectively for a 20 mm annulus (hollow) beam with 10 mm hole, having a frequency of 120 Hz. FIGS. 9I and 9G show the simulated thermal map 918 and the simulated usage map 920, respectively for a 10 mm circular (not hollow) beam having a frequency of 240 Hz.

Figure 9J:
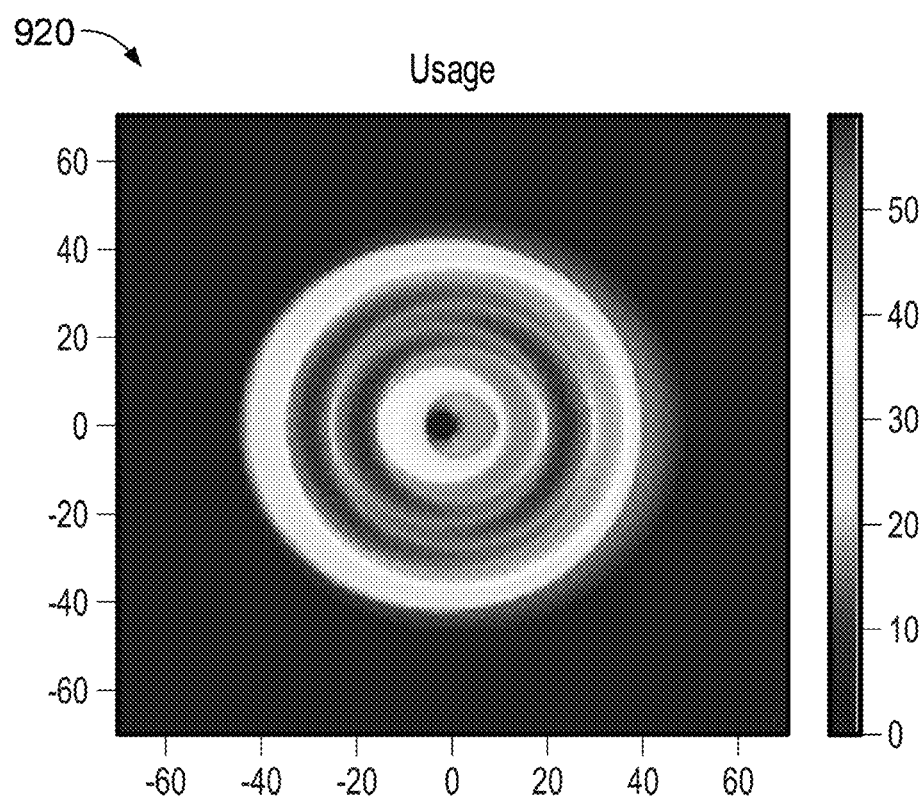

Table 3 shows the simulation results for multiple beam profiles and raster patterns that enable a comparison between the percentage of usage and peak temperature ($T_{max}$) as determined using the model described with reference to FIGS. 5A and 5B. The data was generally analyzed to determine optimal beam profiles and raster patterns. For example, the results of the simulations as illustrated in FIGS. 9A and 9C indicated that a 20 mm beam exhibits an even temperature distribution overall. The results of the simulations as illustrated in FIGS. 9B and 9D indicated that a 10 mm beam exhibits more uniform usage, particularly near the edges. The simulated thermal map 910 and the usage map 912 corresponding to the elliptical beam, as illustrated in FIGS. 9E and 9F, respectively show an increased coverage along the orientation of the major axis of the elliptical beam. Comparing the results of the simulations as illustrated in FIGS. 9E and 9F to the results of the simulations as illustrated in FIGS. 9A and 9B indicates that an elliptically shaped beam with approximately the same area as a circular beam produces less even temperature and usage distributions than the circular beam. The simulated thermal map 914 and the usage map 916 corresponding to the annulus beam, as illustrated in FIGS. 9G and 9H, respectively show a decreased peripheral coverage with uneven radial distribution. Comparing the results of the simulations as illustrated in FIGS. 9G and 9H to the results of the simulations as illustrated in FIGS. 9A and 9B indicates that using any kind of beam with a hole decreases efficiency and produces a more uneven temperature distribution throughout the target. Comparing the results of the simulations as illustrated in FIGS. 9I and 9J to the results of the simulations as illustrated in FIGS. 9A and 9B indicates that using a 240 Hz beam produces a more even temperature distribution throughout the target and similar target usage.

TABLE 3

| Profile Parameters | CS 240 Hz | CS 240 Hz | CS 240 Hz | CS 240 Hz | CS 120 Hz | RPA 240 Hz |
| --- | --- | --- | --- | --- | --- | --- |
| Beam Parameters (diameter) | 20 mm | 10 mm | 15 × 25 mm elliptical | 20 mm with 10 mm hole | 20 mm | 20 mm |
| % Usage | 58.8% | 56% | 58.3% | 57.8% | 59.2% | 68.4% |
| $T_{max}$ | 148° C. | 178° C. | 152° C. | 152° C. | 162° C. | 139° C. |

Figure 10:
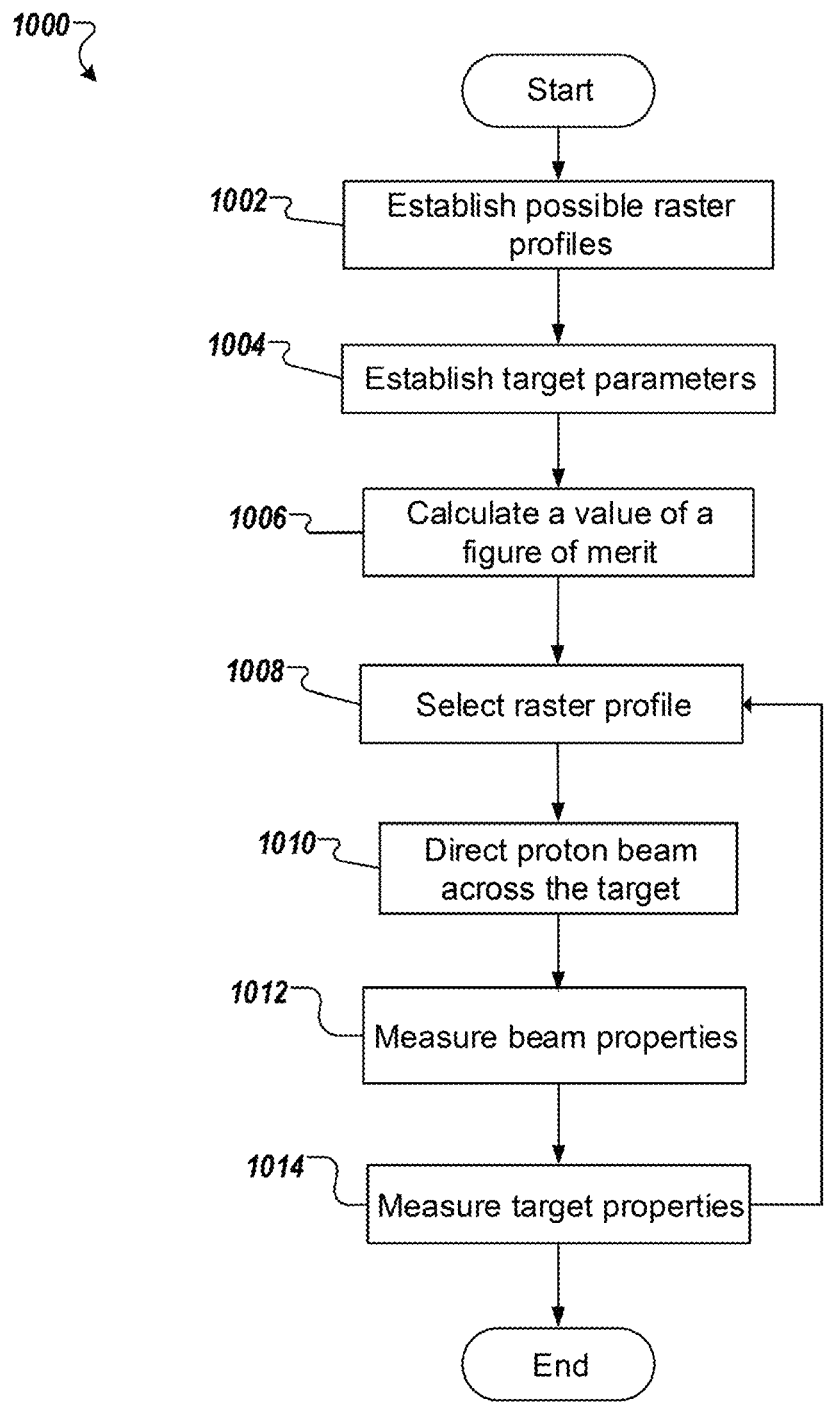
FIG. 10 is a flowchart depicting an example process that can be executed in accordance with implementations of the present disclosure.

FIG. 10 is a flowchart depicting an example process 1000 that can be executed in accordance with implementations of the present disclosure. A variety of possible raster profiles for scanning a proton beam across the target is established using a computer processing system (1002). Each raster profile defines a different scanning pattern of a target. Each scanning pattern includes multiple super cycles that form a closed path on the target surface based on one or more cycles to close the loop. The scanning pattern can include a RPA pattern (e.g., trochoid shape including multiple lobes) as described with reference to FIGS. 7A-7D or other scanning patterns described above. The scanning pattern can be characterized by one or more path parameters. In some implementations, the parameters include one or more of the following parameters: an angular frequency associated with each lobe of the path of the proton beam, a linear velocity of the proton beam across a surface of the target, a number of radial scan layers in a super cycle of the path of the proton beam, a traversal order of the lobes, and a number of super cycles of the path of the proton beam. The angular frequency and the angular velocity of the proton beam can vary for different lobes of the RPA pattern. The traversal order of the lobes can be a forward order, a reverse order or a coprime order. The path parameters characterize the path of the proton beam across the target. The path parameters of the selected raster profile define a path for the proton beam having a minimum delay (exceeding a threshold period) between successive exposures of a single location of the target to the proton beam to minimize target damaging. In some implementations, the possible raster profiles include a masked profile that can be formed based on real time measurements based on imaging data (e.g., thermal maps of the target). The masked profile can define a scan profile configured to avoid portions of the target including weak areas (e.g., areas heated near to the melting point) or damaged regions of the scannable area of the target.

In addition to a scanning pattern, each of the raster profiles includes settings for one or more beam parameters. Each of the beam parameters characterizes a property of the proton beam. The beam parameters can include one or more of the following parameters: a beam dimension (e.g., a diameter of a circular beam), a beam shape, and a beam structure. In some implementations, the beam dimension is in a range from 10 mm to 30 mm Raster profiles can be modified with a normalization coefficient in the X and Y direction depending to the beam shape. The beam shape can be circular or elliptical. If the beam shape is elliptical, the scan can be modified to change effectively by lowering the scan radius in the direction that the beam is the largest so that the beam does not scan outside the outer boundary. The structure of the beam refers to the beam intensity distribution across its cross section. In some implementations, the distribution can be substantially constant or Gaussian. In certain implementations, the distribution can have more than one peak, such as for an annular beam structure.

One or more target parameters characterizing the target are also established using the computer processing system (1004). For example, the target parameters can include of: target surface area, target thickness, and/or target composition.

A value of a figure of merit is calculated for each of the possible beam raster profiles (1006). Generally, the figure of merit is based on a thermal loading of the target by the proton beam for the corresponding possible raster profile. In some implementations, calculating the values for the figure of merit includes, for each of the possible raster profiles, calculating a thermal load at each of a plurality of discrete portions of the target based on a linear relationship between the thermal load and a proton flux at each discrete portion for the corresponding raster profile. In some implementations, each discrete portion corresponds to an area of a surface of the target in the path of the proton beam that is smaller than a dimension of the proton beam. In some implementations, the thermal load at each discrete portion is calculated based on heat transfer through a depth of the target away from a surface of the target on which the proton beam is incident. In some implementations, the figure of merit is selected from the group consisting of: a peak temperature of the target, a temperature change of the target, an average temperature of the target, and a usage efficiency of the target.

A raster profile is selected from among the possible raster profiles based on the value of the figure of merit and based on the measured property of the target (1008). In some implementations, the selection of the raster profile includes a presentation of an operator of the proton beam with a list of the possible raster profiles and receiving, via a user interface of the computer system, a user input including a selection from the list by the operator. In some cases, raster profile selection can occur automatically, e.g., based on measurements of either the beam properties, target properties, or both. For instance, where a threshold level of heating is detected on the target, the system can switch to a different raster profile that puts less stress on the location where the threshold load is detected. In some implementations, the system uses an active feedback or feedforward process and periodically adjusts the raster profile to prolong the useful life of the target.

In some implementations, multiple raster profiles can be selected as candidate profiles, $F_k(t)$, and cutover functions, $s_k(t)$, can be applied to switch between profiles. The output profile, $F(t)$, can be defined by:

$$F(t)=\Sigma_{k=1}^{n} s_k(t) F_k(t),$$

where $\Sigma_{k=1}^{n} s_k(t)=1$ for every value t in the domain of the output profile.

For example, a simple linear crossover between two profiles, F1(t) and F2(t), starting at t1 and ending at t2 could be described by defining s1(t) and s2(t) as follows:

$$s_1(t) = \begin{cases} 1 & t < t_1 \\ 1 - \dfrac{t-t_1}{t_2-t_1} & t_1 \le t \le t_3 \\ 0 & t > t_2 \end{cases}$$

$$s_2(t) = \begin{cases} 0 & t < t_1 \\ 0 + \dfrac{t-t_1}{t_2-t_1} & t_1 \le t \le t_2 \\ 1 & t > t_2 \end{cases}$$

After selection of a particular raster profile, the proton beam is scanned across the target according to the selected raster profile (1010).

One or more properties of the beam are measured (1012) as part of process 1000. In some implementations, the properties of the beam are measured upstream from the target. The beam properties that can be measured include, for example, a beam size, a beam structure, and a beam profile, as described with reference to FIGS. 9A-9J. The beam profile can be measured using infrared cameras configured to determine the beam shape at the target location.

One or more properties of the target are measured (1014) as part of process 1000. In some implementations, the one or more properties of the target include a temperature of the target at one or more locations across the target. For example, one or more thermal sensors (e.g., infrared cameras) can detect the temperature of the target at a corresponding location. In some implementations, a temperature map of the target can be acquired by a thermal camera. The measured temperature can be used as an input to dynamically adjust or change the raster profile during the scanning process to avoid local overheating of the target. In some cases, the system can pause beam operation entirely to avoid overheating the target and resume operation once the target cools to an acceptable level.

Thus, implementations of the present disclosure can include a number of advantages. In some examples, the described techniques provide accurate estimations of target heating and usage with minimized computation resource requirements. Designs described herein illustrate advantages of particular raster profiles and beam profiles that can extend the lifetime of a target, by maintaining peak temperature under the damaging (e.g., blistering) temperature of the target. The described implementations can also enable an improved performance of BNCT, by providing an even distribution of particle loading on the target, which positively affects the profile of the particle beam that irradiates the patient.

In one aspect . . . [the attorneys will include a claims bank here once the claims are finalized]

Figure 11:
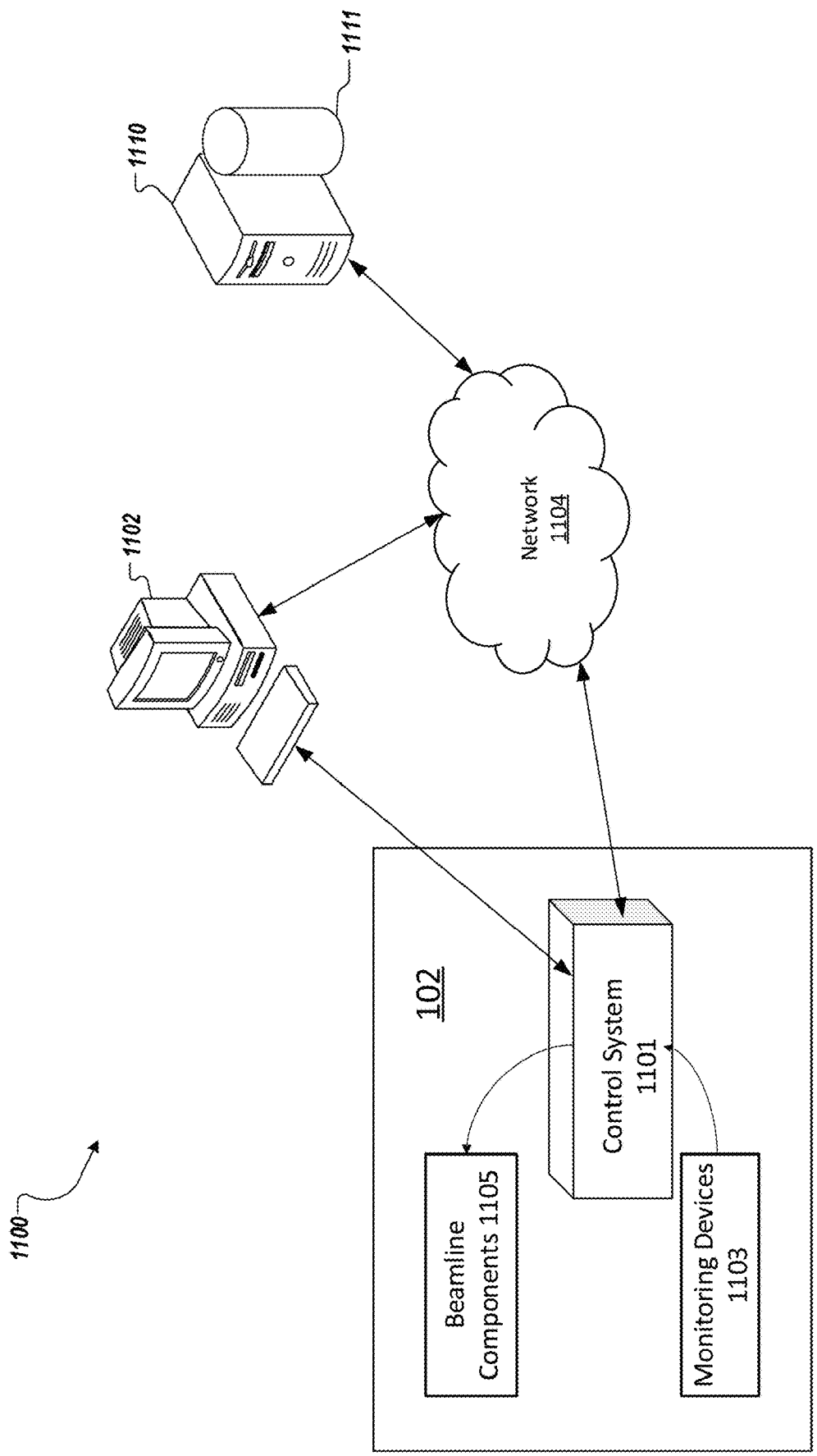
FIG. 11 is an example system that can be implemented in accordance with the present disclosure.

FIG. 11 is a block diagram showing an example system that can be implemented in accordance with the present disclosure. For example, the illustrated example system 1100 includes a beam system 102 one or more computing devices 1102, and one or more servers 1110. In some implementations, beam system 102 may be part of an example neutron beam system (e.g., system 102 described with reference to FIGS. 1A and 1B). The beam system 102 may employ one or more control systems 1101 with which one or more computing devices 1102 may communicate in order to interact with the systems and components of the beam system 102 (e.g., neutron beam system 102). The control system 1101 can be programmed to control the steering devices (e.g., magnets, X-Y shifter) in HEBL 50 that determine the X-Y position of the proton beam incident upon the scannable surface 210 of target 196. The beam system 102, the one or more computing devices 1102, and one or more servers 1110 are configured to communicate directly with one another or via a local network, such as network 1104.

Control system 1101 can be programmed with parameters of amplitude and offset controls that allow a fixed displacement of the beam to control location of the total scanned pattern. In some embodiments, the parameters are programmed in or for a digital signal processor (DSP) that controls the magnet power supply. The amplitude and offset parameters can be input to the DSP in real time during operation, i.e., on the fly, to correct for changes in the beam behavior or energy. The real time parameters can form a generalized method of active feedback for ion particle beam control.

Computing devices 1102 may be embodied by various user devices, systems, computing apparatuses, controllers, and the like. For example, a first computing device 1102 may be a desktop computer associated with a particular user, while another computing device 1102 may be a laptop computer associated with a particular user, and in yet another computing device 1102 may be a mobile device (e.g., a tablet or smart device). Each of the computing devices 1102 may be configured to communicate with the beam system 102, for example through a user interface accessible via the computing device. For example, a user may execute a desktop application on the computing device 1102, which is configured to communicate with the beam system 102.

By using a computing device 1102 to communicate with beam system 102, a user may provide operating parameters for beamline components 3005 (e.g., operating voltages, and the like) according to embodiments described herein.

The control system 1101 may be configured to receive measurements, signals, or other data from components 1105 and monitoring devices 1103 of the beam system 102. For example, the control system 1101 may receive signals from one or more monitoring devices 1103 indicative of operating conditions and/or a position of a beam passing through the beam system 102. The control system 1101, depending on the operating conditions and/or position of the beam passing through the beam system 102, may provide adjustments to inputs of one or more beam line components 1105 according to the methods described herein. The control system 1101 may also provide information collected from any of the components of the beam system 102, including the monitoring devices 1103, to the computing device 1102 either directly or via communications network 1104. The control system 1101 can be programmed to implement embodiments of the scanning profile as described with reference to FIGS. 4, 5, and 7-10.

The communications network 1104 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communications network 1104 may include an 802.11, 802.16, 802.20, and/or WiMax network. The communications network 1104 may include a public network, such as the Internet, a private network, such as an intranet, or combinations thereof, and may utilize a variety of networking protocols now available or later developed including, but not limited to TCP/IP based networking protocols. The computing device 1102 and control system 1101 may be embodied by one or more computing systems, such as system 1200 described with reference to FIG. 12.

The computing device 1102 and control system 1101 can be configured to perform operations comprising scanning the beam across a scannable surface of a target along a first path; and scanning the beam across the scannable surface of the target along a second path, wherein the first path forms a first pattern at a first radial orientation, and the second path forms substantially the first pattern at a second radial orientation different from the first radial orientation. The beam is pulsed while scanning along the first and second paths. The beam continuously propagates while scanning along the first and second paths. The beam moves from an inner region to an outer region of the scannable surface and back to the inner region in the first pattern. The beam moves from an outer region to an inner region of the scannable surface and back to the outer region in the first pattern. The first pattern comprises a spiral and a mirror image of the spiral. The first pattern has a first half and a second half, wherein the first and second halves are symmetrical. The first pattern is continuously curved. The first pattern has a start location and a stop location, wherein the start location is at or adjacent to the stop location. The first radial orientation differs from the second radial orientation by 180 degrees. The operations further comprising: scanning the beam across the scannable surface of the target along a third path, wherein the third path forms the first pattern at a third radial orientation different from the first and second radial orientations. The first, second, and third radial orientations differ by 120 degrees. The operations further comprising: scanning the beam across the scannable surface of the target along a fourth path, wherein the fourth path forms the first pattern at a fourth radial orientation different from the first, second, and third radial orientations. The first, second, third, and fourth radial orientations differ by 90 degrees. The operations further comprising: scanning the beam across the scannable surface of the target along a fifth path, wherein the fifth path forms the first pattern at a fifth radial orientation different from the first, second, third, and fourth radial orientations. The first, second, third, fourth, and fifth radial orientations differ by 72 degrees. The first path corresponds to a first instance of a cycle, and the second path corresponds to a second instance of the cycle. In some implementations, scanning of the first instance of the cycle and the second instance of the cycle forms a closed loop. The beam is a proton beam. The scannable surface is a lithium or beryllium surface. The target generates neutrons when scanned. The beam has a circular cross-sectional profile. The beam has an elliptical cross-sectional profile. The beam has an annular cross-sectional profile. The beam has a hollow cross-sectional profile. The operations performing a boron neutron capture therapy (BNCT). The beam is generated by a beam system comprising: an ion source; a first beamline coupled with the ion source; a tandem accelerator coupled with the first beamline; a second beamline coupled with the tandem accelerator; and the target coupled with the second beamline The pattern exposes a majority of the scannable surface to the beam. The second path forms the first pattern at the second radial orientation different from the first radial orientation.

The computing device 1102 and control system 1101 can be configured to perform operations comprising scanning the beam across a scannable surface of a target along a first path; and scanning the beam across the scannable surface of the target along a second path, wherein the first path forms a first pattern at a first radial orientation, and the second path forms a second pattern at a second radial orientation different from the first radial orientation, wherein the first and second patterns are substantially the same but for the different radial orientations. The first and second patterns are the same but for the different radial orientations.

The computing device 1102 and control system 1101 can be configured to perform operations comprising establishing, using a computer processing system, a plurality of possible raster profiles for scanning the proton beam across the target, each of the plurality of possible raster profiles comprising one or more beam parameters, each of the one or more beam parameters characterizing a property of the proton beam and one or more path parameters characterizing a path of the proton beam across the target; establishing, using the computer processing system, one or more target parameters characterizing the target; calculating, using the computer processing system, a value of a figure of merit for each of the possible beam raster profiles, wherein the figure of merit is based on a thermal loading of the target by the proton beam for the corresponding possible raster profile; selecting, using the computer processing system, a raster profile from among the plurality of plurality of possible raster profiles based on the value of the figure of merit; and directing the proton beam across the target according to the selected raster profile. Calculating the values for the figure of merit comprises, for each of the possible raster profiles, calculating a thermal load at each of a plurality of discrete portions of the target based on a linear relationship between the thermal load and a proton flux at each discrete portion for the corresponding raster profile. Each discrete portion corresponds to an area of a surface of the target in the path of the proton beam that is smaller than a dimension of the proton beam. The thermal load at each discrete portion is calculated based on heat transfer through a depth of the target away from a surface of the target on which the proton beam is incident. The figure of merit is selected from the group consisting of: a peak temperature of the target, a temperature change of the target, an average temperature of the target, and a usage efficiency of the target. The one or more beam parameters are selected from the group consisting of: a beam dimension, a beam shape, and a beam structure. The beam dimension is in a range from 10 mm to 30 mm. The beam shape is circular or elliptical. A structure of the beam is circular or annular. The one or more path parameters is selected from the group consisting of: a frequency associated with the path of the proton beam, a linear velocity of the proton beam across a surface of the target, a number of radial scan layers in a super cycle of the path of the proton beam, and a number of super cycles of the path of the proton beam. The one or more target parameters are selected from the group consisting of: target surface area, target thickness, and target composition. The target comprises a layer of lithium or a layer of beryllium. The target comprises a layer of a metal supporting the layer of lithium or the layer of beryllium. Selecting comprises presenting an operator of the proton beam with a list of the possible raster profiles and receiving, via the computer system, a selection from the list by the operator. The operations further comprising measuring one or more properties of the target and selecting the raster profile based on the measured property of the target. The one or more properties of the target comprise a temperature of the target at one or more locations on the target. The operations, further comprising measuring one or more properties of the beam and selecting the raster profile based on the measured property of the beam. The one or more properties of the beam are measured upstream from the target. The selected raster profile defines a path for the proton beam having a minimum delay between successive exposures of a single location of the target to the proton beam exceeds a threshold period. The selected raster profile defines a path based on a trochoid shape. The trochoid shape comprises a plurality of lobes. The angular frequency of the proton beam varies for different lobes of the trochoid shape. The selected raster profile comprises a varying angular velocity of the proton beam across the target surface. The selected raster profile comprises a varying linear velocity of the proton beam across the target surface.

The computing device 1102 and control system 1101 can be configured to perform operations comprising monitoring a temperature of a target while scanning a proton beam across a surface of the target according to a first raster profile; and based on the monitored temperature, changing the scanning from the first raster profile to a second raster profile, wherein the second raster profile and the first raster profile result in differing heating profiles of the target according to a computer model of a thermal loading of the target by the first and second raster profiles. The scanning is changed in response to selection of the second raster profile from among a plurality of raster profiles by a human operator of the proton beam. The scanning is changed automatically according to a feedback or feedforward algorithm. The temperature is monitored at multiple discrete locations of the target. The temperature is monitored by obtaining a thermal image of the target.

The computing device 1102 and control system 1101 can be configured to perform operations comprising scanning a charged particle beam across a scannable surface of a target in a super cycle, wherein the super cycle comprises a plurality of cycles, each cycle of the plurality of cycles having the same shape and a different azimuthal orientation, wherein the plurality of cycles are concatenated together such that a path of the charged particle beam traverses the plurality of cycles in a closed loop. The plurality of cycles comprises two cycles azimuthally offset by 180 degrees from each other. The plurality of cycles comprises three cycles azimuthally offset by 120 degrees from each other. The plurality of cycles comprises four cycles azimuthally offset by 90 degrees from each other.

Figure 12:
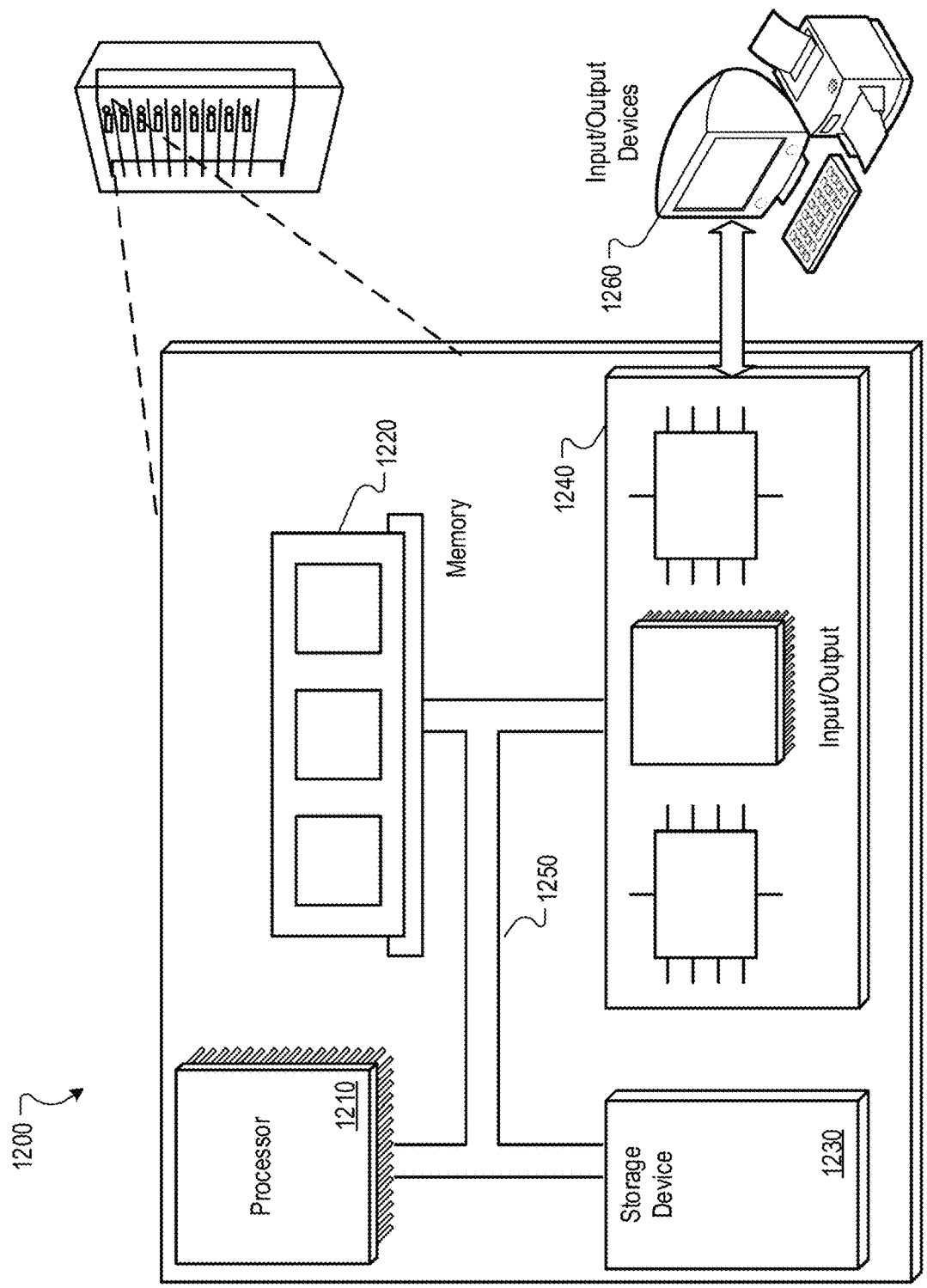
FIG. 12 is a schematic illustration of example computer systems that can be used to execute implementations of the present disclosure.

Referring now to FIG. 12, a schematic view of an example computing system 1200 is provided. The system 1200 can be used for the operations described in association with the implementations described herein. For example, the system 1200 may be included in any or all of the server components discussed herein. The system 1200 includes a processor 1210, a memory 1220, a storage device 1230, and an input/output device 1240. Each of the components 1210, 1220, 1230, and 1240 are interconnected using a system bus 1250. The processor 1210 is capable of processing instructions for execution within the system 1200. In one implementation, the processor 1210 is a single-threaded processor. In another implementation, the processor 1210 is a multi-threaded processor. The processor 1210 is capable of processing instructions stored in the memory 1220 or on the storage device 1230 to display graphical information for a user interface on the input/output device 1240.

The memory 1220 stores information within the system 1200. In one implementation, the memory 1220 is a computer-readable medium. In one implementation, the memory 1220 is a volatile memory unit. In another implementation, the memory 1220 is a non-volatile memory unit. The storage device 1230 is capable of providing mass storage for the system 1200. In one implementation, the storage device 1230 is a computer-readable medium. In various different implementations, the storage device 1230 may be a floppy disk device, a hard disk device, an optical disk device, or a tape device. The input/output device 1240 provides input/output operations for the system 1200. In one implementation, the input/output device 1240 includes a keyboard and/or pointing device. In another implementation, the input/output device 1240 includes a display unit for displaying graphical user interfaces.

In some implementations, two components may both leverage use of the same processor, network interface, storage medium, or the like to perform their associated functions, such that duplicate hardware is not required for each device. The use of the terms "device" and/or "circuitry" as used herein with respect to components of the apparatus therefore can encompass particular hardware configured with software to perform the functions associated with that particular device, as described herein.

The terms "device" and/or "circuitry" should be understood broadly to include hardware, in some embodiments, device and/or circuitry may also include software for configuring the hardware. For example, in some embodiments, device and/or circuitry may include processing circuitry, storage media, network interfaces, input/output devices, and the like. In some implementations, other elements of the system 1200 may provide or supplement the functionality of a particular component(s).

In some embodiments, the processor 1210 (and/or co-processor or any other processing circuitry assisting or otherwise associated with the processor) may be in communication with the memory 1220 via a bus for passing information among components of the apparatus. The memory 1220 may be non-transitory and may include, for example, one or more volatile and/or non-volatile memories. In other words, for example, the memory 1220 may be an electronic storage device (e.g., a computer readable storage medium). The memory 1220 may be configured to store information, data, content, applications, instructions, or the like, for enabling the system 1200 to carry out various functions in accordance with example embodiments of the present disclosure, as described with reference to FIGS. 1-11.

The processor 1210 may be embodied in a number of different ways and may, for example, include one or more processing devices configured to perform independently. Additionally or alternatively, the processor 1210 may include one or more processors configured in tandem via a bus to enable independent execution of instructions, pipelining, and/or multithreading. The use of the terms "processing device" and/or "processing circuitry" may be understood to include a single core processor, a multi-core processor, multiple processors internal to the apparatus, and/or remote or "cloud" processors.

In some implementations, the processor 1210 may be configured to execute instructions stored in the memory 1220 or otherwise accessible to the processor. Alternatively or additionally, the processor 1210 may be configured to execute hard-coded functionality. As such, whether configured by hardware or software methods, or by a combination of hardware with software, the processor may represent an entity (e.g., physically embodied in circuitry) capable of performing operations according to an embodiment of the present disclosure while configured accordingly. Alternatively, as another example, when the processor 1210 is embodied as an executor of software instructions, the instructions may specifically configure the processor 1210 to perform the algorithms and/or operations described herein when the instructions are executed. The instructions can include those necessary to determine a scanning profile and scan a target, as described with reference to FIGS. 1-11.

In some implementations, the system 1200 may include input/output device 1260 that may, in turn, be in communication with processor 1210 to provide output to the user and, in some embodiments, to receive input from the user. The input/output device 1260 may include a user interface and may include a device display, such as a user device display, that may include a web user interface, a mobile application, a client device, or the like. In some embodiments, the input/output device 1260 may also include a keyboard, a mouse, a joystick, a touch screen, touch areas, soft keys, a microphone, a speaker, or other input/output mechanisms. The processor and/or user interface circuitry including the processor may be configured to control one or more functions of one or more user interface elements through computer program instructions (e.g., software and/or firmware) stored on a memory accessible to the processor (e.g., memory 1220, and/or the like).

The communications device or circuitry 1240 may be any means such as a device or circuitry embodied in either hardware or a combination of hardware and software that is configured to receive and/or transmit data from/to a network and/or any other device or circuitry in communication with the system 1200. The communications device or circuitry 1240 may include, for example, a network interface for enabling communications with a wired or wireless communication network. For example, the communications device or circuitry 1240 may include one or more network interface cards, antennas, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s). The signals may be transmitted by the system 1200 using any of a number of wireless personal area network (PAN) technologies, such as current and future Bluetooth standards (including Bluetooth and Bluetooth Low Energy (BLE)), infrared wireless (e.g., IrDA), FREC, ultra-wideband (UWB), induction wireless transmission, or the like. In addition, it should be understood that the signals may be transmitted using Wi-Fi, Near Field Communications (NFC), Worldwide Interoperability for Microwave Access (WiMAX), or other proximity-based communications protocols.

Any such computer program instructions and/or other type of code may be loaded onto a computer, processor, or other programmable apparatus' circuitry to produce a machine, such that the computer, processor, or other programmable circuitry that executes the code on the machine creates the means for implementing various functions, including those described herein.

Embodiments of the present disclosure may be configured as systems, methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Processing circuitry in accordance with the present disclosure can include one or more processors, microprocessors, controllers, and/or microcontrollers, each of which can be a discrete chip or distributed amongst (and a portion of) a number of different chips. Processing circuitry in accordance with the present disclosure can include a digital signal processor, which can be implemented in hardware and/or software of the processing circuitry in accordance with the present disclosure. Processing circuitry in accordance with the present disclosure can be communicatively coupled with the other components of the figures herein. Processing circuitry in accordance with the present disclosure can execute software instructions stored on memory that cause the processing circuitry to take a host of different actions and control the other components in figures herein.

Memory in accordance with the present disclosure can be shared by one or more of the various functional units, or can be distributed amongst two or more of them (e.g., as separate memories present within different chips). Memory can also be a separate chip of its own. Memory can be non-transitory, and can be volatile (e.g., RAM, etc.) and/or non-volatile memory (e.g., ROM, flash memory, F-RAM, etc.).

Computer program instructions for carrying out operations in accordance with the described subject matter may be written in any combination of one or more programming languages and software platforms such as but not limited to Python, Labview platform by National Instruments, Java, JavaScript, Smalltalk, C++, C#, Transact-SQL, XML, PHP or the like and conventional procedural programming languages, such as the "C" programming language or similar programming languages.

Various aspects of the present subject matter are set forth below, in review of, and/or in supplementation to, the described embodiments, with the emphasis here being on the interrelation and interchangeability of the following embodiments. In other words, an emphasis is on the fact that each feature of the embodiments can be combined with each and every other feature unless explicitly stated otherwise or logically implausible.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of operating a beam, comprising:
   scanning the beam across a scannable surface of a target along a first path; and
   scanning the beam across the scannable surface of the target along a second path, wherein the first path forms a first pattern at a first radial orientation, and the second path forms substantially the first pattern at a second radial orientation different from the first radial orientation.

2. The method of claim 1, wherein the beam is pulsed while scanning along the first path and the second path.

3. The method of claim 1, wherein the beam continuously propagates while scanning along the first path and the second path.

4. The method of claim 1, wherein the beam moves from an inner region to an outer region of the scannable surface and back to the inner region in the first pattern.

5. The method of claim 1, wherein the beam moves from an outer region to an inner region of the scannable surface and back to the outer region in the first pattern.

6. The method of claim 1, wherein the first pattern comprises a spiral and a mirror image of the spiral.

7. The method of claim 1, wherein the first pattern has a first half and a second half, wherein the first half and the second half are symmetrical.

8. The method of claim 1, wherein the first pattern has a start location and a stop location, wherein the start location is at or adjacent to the stop location.

9. The method of claim 1, wherein the first radial orientation differs from the second radial orientation by 180 degrees.

10. The method of claim 1, further comprising:
scanning the beam across the scannable surface of the target along a third path, wherein the third path forms the first pattern at a third radial orientation different from the first radial orientation and the second radial orientation.

11. The method of claim 10, wherein the first radial orientation, the second radial orientation, and the third radial orientation differ by 120 degrees.

12. The method of claim 10, further comprising:
scanning the beam across the scannable surface of the target along a fourth path, wherein the fourth path forms the first pattern at a fourth radial orientation different from the first radial orientation, the second radial orientation, and the third radial orientation.

13. The method of claim 12, wherein the first radial orientation, the second radial orientation, the third radial orientation, and the fourth radial orientation differ by 90 degrees.

14. The method of claim 12, further comprising:
scanning the beam across the scannable surface of the target along a fifth path, wherein the fifth path forms the first pattern at a fifth radial orientation different from the first radial orientation, the second radial orientation, the third radial orientation, and the fourth radial orientation, wherein the first radial orientation, the second radial orientation, the third radial orientation, the fourth radial orientation, and the fifth radial orientation differ by 72 degrees.

15. The method of claim 1, wherein the first path corresponds to a first instance of a cycle, and the second path corresponds to a second instance of the cycle, wherein scanning of the first instance of the cycle and the second instance of the cycle forms a closed loop.

16. The method of claim 1, wherein the beam is a proton beam and the scannable surface is a lithium or beryllium surface.

17. The method of claim 1, wherein the target generates neutrons when scanned.

18. The method of claim 1, wherein the beam is scanned across the scannable surface of the target along a plurality of paths, wherein the plurality of paths comprises the first path and the second path, wherein a quantity N of paths in the plurality of paths is two or more, wherein the N paths together form a closed loop, and wherein each of the N paths forms substantially the first pattern radially offset from an adjacent one of the paths by 360/N degrees.

19. The method of claim 1, wherein the beam has a cross-sectional profile that is at least one of circular, elliptical, annular, and hollow.

20. The method of claim 1, wherein the beam is generated by a beam system comprising:
an ion source;
a first beamline coupled with the ion source;
a tandem accelerator coupled with the first beamline;
a second beamline coupled with the tandem accelerator; and
the target coupled with the second beamline.

* * * * *